US009486257B2

(12) United States Patent
Smith

(10) Patent No.: US 9,486,257 B2
(45) Date of Patent: Nov. 8, 2016

(54) ROD REDUCTION TOOL AND METHOD TO ASSIST IN THE PASSAGE OF A CONNECTING ROD BETWEEN PEDICLE SCREWS

(71) Applicant: Jeffrey Scott Smith, Granbury, TX (US)

(72) Inventor: Jeffrey Scott Smith, Granbury, TX (US)

( * ) Notice: Subject to any disclaimer, the term of this patent is extended or adjusted under 35 U.S.C. 154(b) by 31 days.

(21) Appl. No.: 14/821,538

(22) Filed: Aug. 7, 2015

(65) Prior Publication Data

US 2016/0038196 A1 Feb. 11, 2016

Related U.S. Application Data

(60) Provisional application No. 62/034,754, filed on Aug. 7, 2014.

(51) Int. Cl.
*A61B 17/70* (2006.01)
*A61B 17/56* (2006.01)

(52) U.S. Cl.
CPC ....... *A61B 17/7085* (2013.01); *A61B 17/7032* (2013.01); *A61B 17/7083* (2013.01); *A61B 17/7086* (2013.01); *A61B 2017/564* (2013.01)

(58) Field of Classification Search
CPC .......................... A61B 17/70–17/7046; A61B 17/7074–17/7092
See application file for complete search history.

(56) References Cited

U.S. PATENT DOCUMENTS

| 7,179,261 | B2 | 2/2007 | Sicvol et al. |
| 7,306,603 | B2 | 12/2007 | Boehm, Jr. et al. |
| 7,476,240 | B2 | 1/2009 | Raymond et al. |
| 7,527,638 | B2 | 5/2009 | Anderson et al. |
| 7,588,588 | B2 | 9/2009 | Spitler et al. |
| 7,648,506 | B2 | 1/2010 | McCord et al. |
| 7,648,507 | B2 | 1/2010 | Techiera et al. |
| 7,666,188 | B2 | 2/2010 | Anderson et al. |
| 7,708,763 | B2 | 5/2010 | Selover et al. |
| 7,854,751 | B2 | 12/2010 | Sicvol et al. |
| 7,922,727 | B2 | 4/2011 | Songer et al. |
| 7,922,749 | B2 * | 4/2011 | Dewey ............... A61B 17/7086 606/246 |
| 8,075,591 | B2 | 12/2011 | Ludwig et al. |
| 8,105,361 | B2 | 1/2012 | Anderson et al. |
| 8,162,952 | B2 | 4/2012 | Cohen et al. |
| 8,277,491 | B2 | 10/2012 | Selover et al. |
| 8,343,160 | B2 | 1/2013 | Techiera et al. |
| 8,518,082 | B2 | 8/2013 | Sicvol et al. |
| 8,523,916 | B2 | 9/2013 | Anderson et al. |

(Continued)

FOREIGN PATENT DOCUMENTS

WO 2013112689 8/2013

OTHER PUBLICATIONS

Silverbolt MIS Screw System with Multi-level & Dynabolt Rod Options. Exactech Spine, n.d. Web. Based on information and belief, available at least as early as Jan. 19, 2015. <http://exactechspine.com/medical-professionals/operative-technique-library-files/silverbolt-operative-technique>.

(Continued)

*Primary Examiner* — Jan Christopher Merene
*Assistant Examiner* — Steven Cotroneo
(74) *Attorney, Agent, or Firm* — Workman Nydegger

(57) ABSTRACT

Rod delivery tools, methods for delivering a connecting rod of a pedicle screw system into seating slots of at least first and second long arm screw towers of a pedicle screw system, and a rod reduction tool and related methods for urging a distal leading end of a connecting rod and an opening of a long arm screw tower into alignment with one another, where the two are initially misaligned.

11 Claims, 20 Drawing Sheets

(56) References Cited

U.S. PATENT DOCUMENTS

| | | | |
|---|---|---|---|
| 8,556,904 | B2 | 10/2013 | Rezach et al. |
| 8,617,210 | B2 | 12/2013 | Sicvol et al. |
| 8,721,692 | B2 | 5/2014 | Anderson et al. |
| 8,734,490 | B2 | 5/2014 | Anderson et al. |
| 8,920,425 | B2 | 12/2014 | Techiera et al. |
| 2002/0095153 | A1* | 7/2002 | Jones ............ A61B 17/7037 606/86 A |
| 2005/0131419 | A1 | 6/2005 | McCord et al. |
| 2007/0191836 | A1 | 8/2007 | Justis |
| 2007/0270842 | A1* | 11/2007 | Bankoski ........ A61B 17/7076 606/86 A |
| 2008/0077138 | A1 | 3/2008 | Cohen et al. |
| 2008/0154279 | A1* | 6/2008 | Schumacher .... A61B 17/7083 606/104 |
| 2009/0264930 | A1* | 10/2009 | McBride ......... A61B 17/7004 606/250 |
| 2010/0094359 | A1 | 4/2010 | Techiera et al. |
| 2010/0312279 | A1 | 12/2010 | Gephart et al. |
| 2011/0218581 | A1 | 9/2011 | Justis |
| 2011/0313464 | A1* | 12/2011 | McLean .......... A61B 17/708 606/279 |
| 2012/0123487 | A1 | 5/2012 | Mahar |
| 2012/0271365 | A1* | 10/2012 | Daubs ............. A61B 17/7086 606/86 A |
| 2013/0110184 | A1 | 5/2013 | Wing et al. |
| 2013/0296949 | A1 | 11/2013 | Sicvol et al. |
| 2014/0074106 | A1 | 3/2014 | Shin |
| 2014/0163625 | A1 | 6/2014 | Meyer et al. |
| 2014/0222083 | A1 | 8/2014 | Anderson et al. |
| 2014/0222092 | A1 | 8/2014 | Anderson et al. |
| 2014/0277206 | A1 | 9/2014 | Reitblat et al. |
| 2014/0330315 | A1 | 11/2014 | Butler et al. |

OTHER PUBLICATIONS

"Fortex Pedicle Screw System, Simplicity Reinvented." X-spine Systems, Inc. Web. Based on information and belief, available at least as early as Jan. 19, 2015. <http://www.highlandmedical.co.uk/brochures/Fortex-Reduction-Brochure-Rev-A-Reduced.pdf>.

"Isobar Evolution Compression Rod." Alphatec Spine, Inc. Web. Based on information and belief, available at least as early as Jan. 19, 2015. <http://www.implantesclp.com/uploads/pdf/ISOBAR_EVOLUTION.pdf>.

\* cited by examiner

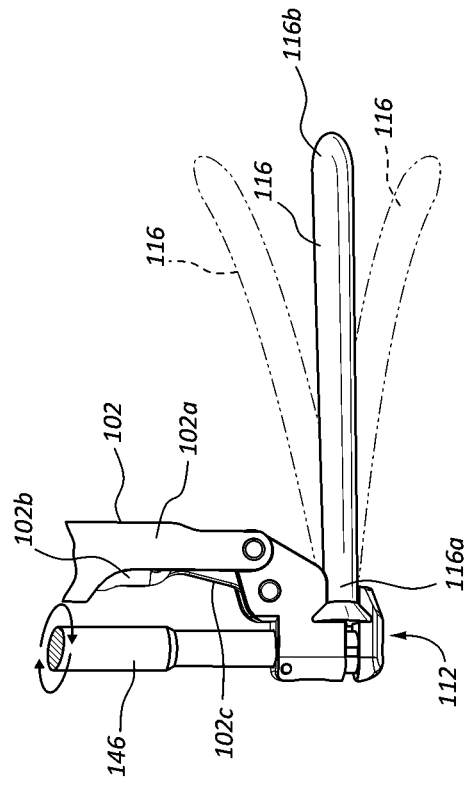
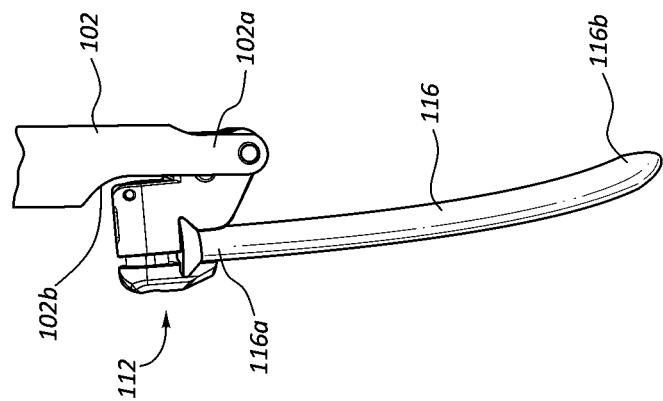
FIG. 2D
FIG. 2C

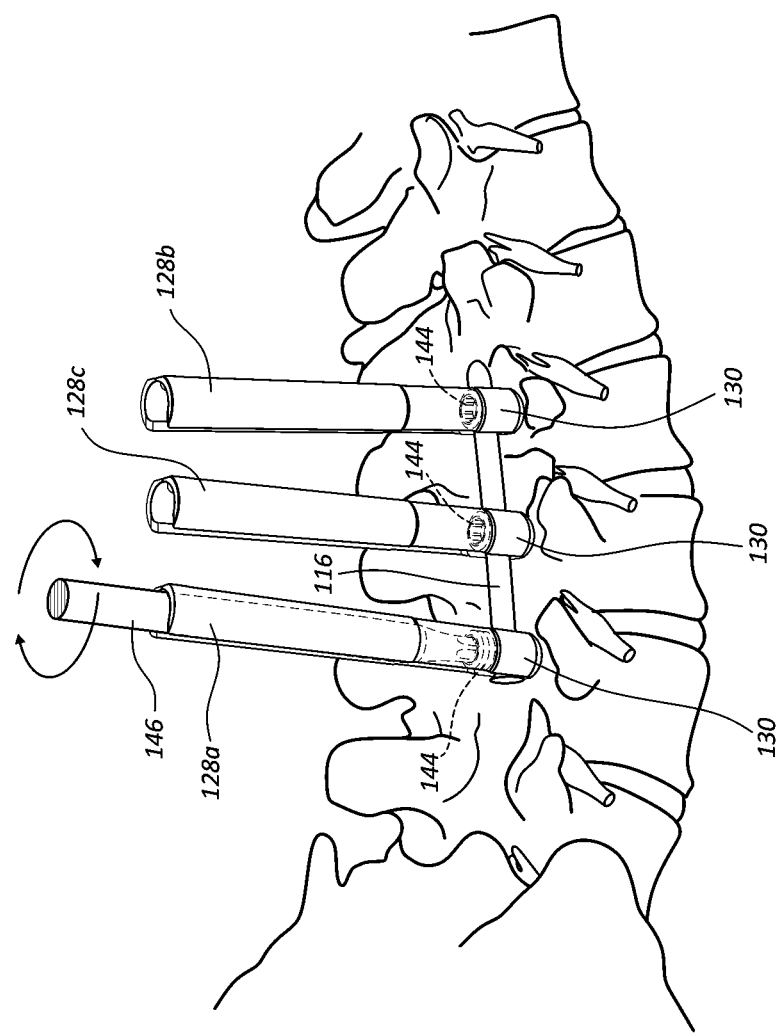

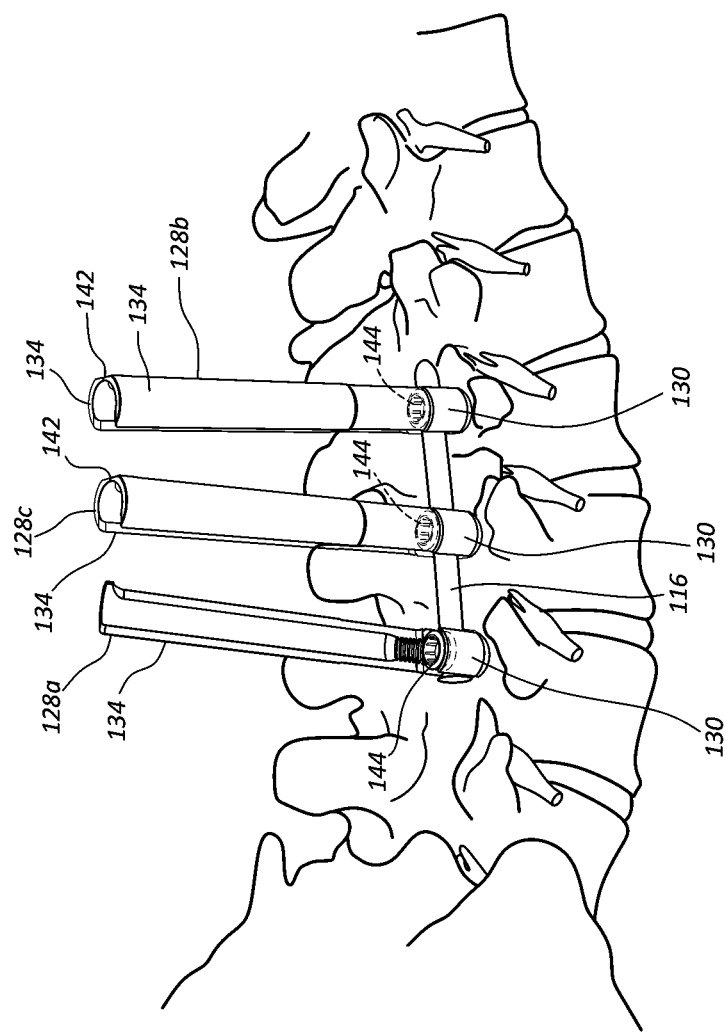

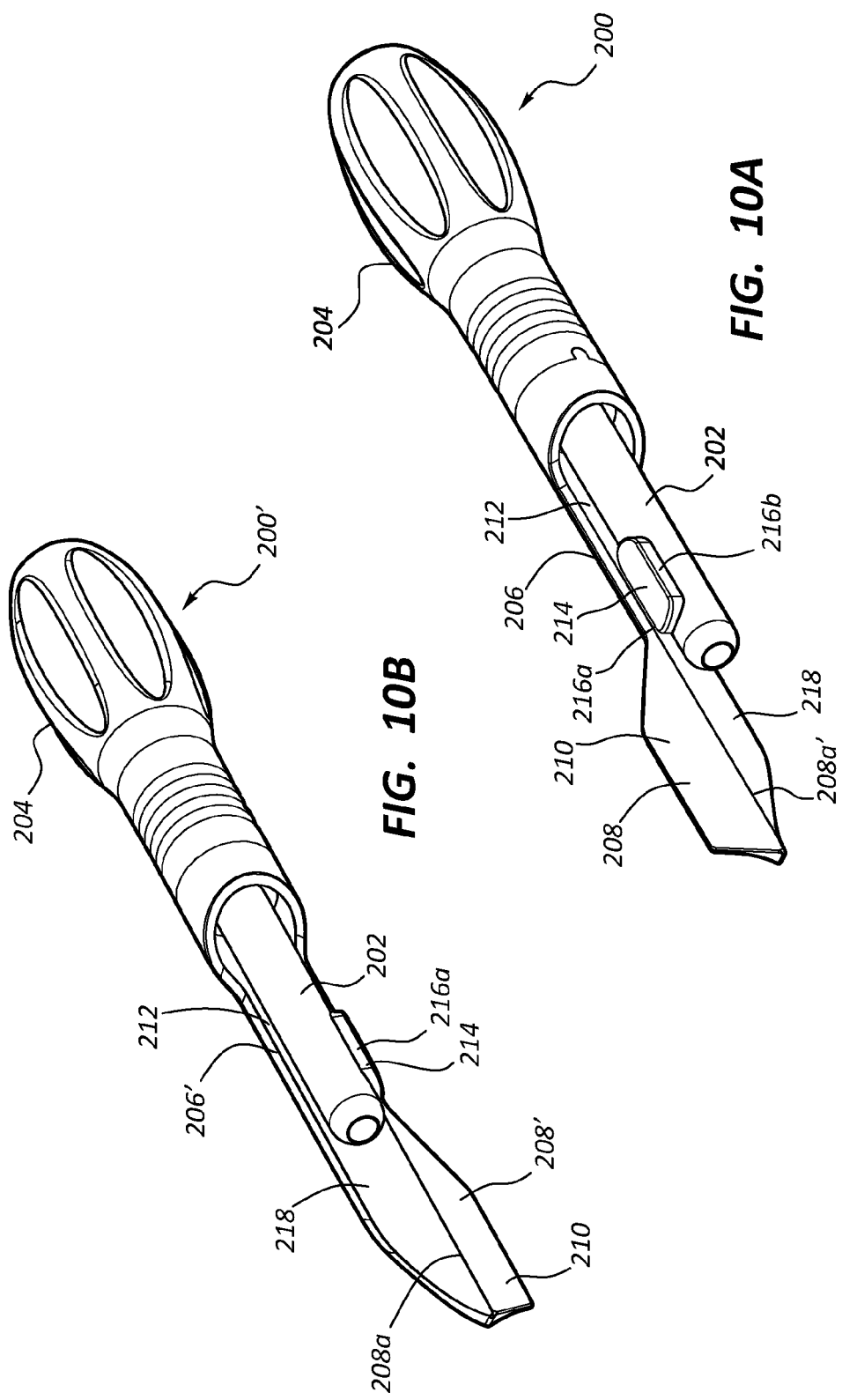

ROD REDUCTION TOOL AND METHOD TO ASSIST IN THE PASSAGE OF A CONNECTING ROD BETWEEN PEDICLE SCREWS

CROSS-REFERENCE TO RELATED APPLICATIONS

The present application claims the benefit under 35 USC §119(e) of U.S. Patent Application Ser. No. 62/034,754, filed Aug. 7, 2014 and entitled "REDUCTION TOOL TO ASSIST IN THE PASSAGE OF A CONNECTING ROD BETWEEN PEDICLE SCREWS", the disclosure of which is incorporated by reference in its entirety. Another application, U.S. Patent Application Ser. No. 62/042,226, filed Aug. 26, 2014 and entitled "ROD DELIVERY TOOL FOR USE IN PEDICLE SCREW SYSTEMS", is also incorporated by reference in its entirety.

BACKGROUND OF THE INVENTION

1. The Field of the Invention

The present invention generally relates to medical devices and methods of use, particularly to pedicle screw systems and methods for their installation.

2. The Relevant Technology

Over the past several decades, spinal surgery has increasingly become an important option available to surgeons and patients in treating issues related to the spine. Because the spine generally provides support and movement for the body, a problem with the spine (e.g., a back disorder) can disrupt even the simplest life activities. In general, thousands of surgical fusions of the spine are performed each year in an attempt to decrease pain and to increase function for the patient. Stabilization of the spine through fusion may be accomplished in a variety of ways, including, for example, the use of pedicle screws, e.g., often used to assist in the fixation of the lumbar and thoracic portions of the spine. Such pedicle screws are generally biocompatible screws that are typically anchored into a vertebra at the pedicle, which is a projection from the body of a given vertebra that connects the body of the vertebra to an arch of the vertebra. Vertebrae generally have two pedicles.

Stability is desired in order to minimize motion while healing occurs, which healing includes fusion of the bone. Pedicle screws have been placed using both traditional open techniques, as well as minimally invasive (e.g., percutaneous) techniques. The placement process itself can be time consuming and difficult. Complexity and difficulty, at least from the perspective of the surgeon, has in some ways been exacerbated by the increased popularity in recent years in the use of minimally invasive techniques for placement of the pedicle screws and associated instrumentation. These techniques generally involve the use of some kind of a percutaneous access device (PAD) which attaches to the pedicle screw, or may be an extension of the screw itself. The PAD allows the surgeon to pass a rod down through the PAD and into the accepting heads of the implanted pedicle screws so that the screws can be connected to each other, forming a composite structure capable of stabilizing that portion of the spine. The connecting rod is generally secured to the pedicle screws by locking nuts which may be inserted through the PADs and tightened. The PADs may eventually be removed.

Many methods have been employed to facilitate delivery and passage of the connecting rod down through a PAD to each respective pedicle screw, although alignment of the connecting rod, so that it is secured to each pedicle screw, has proven to often be a challenge for even the most experienced surgeons. Passing a connecting rod, without direct visualization, through the appropriate receiving head of each successive screw requires precision, patience, and on occasion, a little luck. The reasons for this are that the receiving heads attached to or part of the top of the pedicle screws are typically only slightly larger in diameter than the connecting rod itself. In some cases, clearance between the two is less than a millimeter. As such, even with a rod having a tapered end, proper alignment, insertion, and seating of the rod can be frustrating.

Where only two pedicle screws are to be spanned by the connecting rod, this task may be more readily feasible, as a straight line connects two points. Where three or more pedicle screws are to be spanned by the connecting rod, the process becomes much more difficult, as the three or more screws are rarely on the same line. All too often, one or more of the screws in such an arrangement is enough out of alignment that the surgeon is unable to pass the rod through all of the receiving heads without increasing exposure (i.e., additional incisions) to the surgical site, to provide for direct visualization. It will be apparent that there exists a continuing need for improved methods for delivering such connecting rods, and associated devices used in delivery of the connecting rod.

BRIEF SUMMARY

In one aspect, the present invention relates to methods for delivering a connecting rod of a pedicle screw system into seating slots of at least first and second long arm screw towers of a pedicle screw system, e.g., after pedicle screws of the pedicle screw system have been placed into pedicles of a patient's vertebrae. Such a method may include attaching a proximal end of the connecting rod to a rod delivery tool through a clamping mechanism of the rod delivery tool; providing an incision adjacent to a first long arm screw tower, which incision provides a pathway through which at least a portion of the connecting rod is delivered to the pedicle screw system; and inserting an elongate shaft of the rod delivery tool through the first long arm screw tower. Such insertion may result in at least a portion of the connecting rod remaining outside of the first long arm screw tower as the connecting rod is advanced towards the pedicle screws at the distal ends of the long arm screw towers. For example, the proximal (e.g., "heel") end of the connecting rod may be progressively advanced towards a pedicle screw at a distal end of a first long arm screw tower, while the distal leading end of the connecting rod may be progressively advanced towards a pedicle screw at the distal end of the second (i.e., "last") long arm screw tower. The connecting rod may be in a first orientation relative to the elongate shaft of the rod delivery tool during at least a first portion of advancement as the connecting rod is advanced towards the pedicle screws at the distal ends of the first and second long arm screw towers.

Once the distal leading end of the connecting rod reaches a desired position, the connecting rod may be pivoted from the first orientation to a second orientation so that the connecting rod passes through both the first and second long arm screw towers. The method may further include advancing a locking nut associated with the second long arm screw tower distally (e.g., downward) through the second long arm screw tower, over the distal leading end of the connecting rod, to secure the distal leading end of the connecting rod into the seating slot of the second long arm screw tower. The proximal end of the connecting rod may be released from the clamping mechanism of the rod delivery tool, and the rod delivery tool may be withdrawn from the first long arm screw tower. A locking nut associated with the first long arm screw tower may be advanced distally through the first long arm screw tower, over the proximal end of the connecting rod to secure the proximal end of the connecting rod into the seating slot of the first long arm screw tower. In an embodiment, the steps described above may be performed in the order described. In some embodiments, it may be possible to rearrange the order of at least some of the steps.

In some embodiments, a third long arm screw tower may be present, e.g., between the first long arm screw tower (into which the proximal heel end of the connecting rod is eventually seated) and the second (i.e., "last") long arm screw tower, into which the distal leading end of the connecting rod is eventually seated.

In another aspect, the present invention is directed to a rod delivery tool for delivering a connecting rod of a pedicle screw system into seating slots of adjacent long arm screw towers of the pedicle screw system. Such a rod delivery tool may include an elongate shaft extending between proximal and distal ends, the elongate shaft being configured for receipt into a longitudinal channel of a long arm screw tower during use. The tool may include a handle at a proximal end of the elongate shaft, the handle including an actuating mechanism (e.g., a trigger) for pivoting a clamping mechanism (and a connecting rod clamped therein) at the distal end of the shaft from a first orientation (e.g., employed during downward advancement of the connecting rod towards the pedicle screws) to a second orientation (e.g., in which the connecting rod passes through the long arm screws).

The tool may include a clamping mechanism at the distal end of the elongate shaft for clamping over the connecting rod, where the actuating mechanism is configured to selectively pivot the clamping mechanism from the first orientation to the second orientation. The tool may include one or more alignment guides disposed along a length of the elongate shaft for reception of a driver, for adjusting the clamping mechanism (e.g., a screw thereof) to provide selective clamping and release of the connecting rod in the clamping mechanism.

Another aspect of the present disclosure relates to a rod reduction tool for urging a connecting rod into alignment with a long arm screw tower of a pedicle screw system, where the connecting rod is initially misaligned for passage through an opening in the sidewall of the long arm screw tower. Such a rod reduction tool may include an elongate shaft extending from a proximal handle portion, the elongate shaft being configured (e.g., sized and shaped) for insertion into a longitudinal channel of a long arm screw tower during use. An alignment extension member including a paddle at a distal end thereof may also extend from the proximal handle portion. The paddle may be configured (e.g., sized and positioned) to engage and press the distal leading end of a connecting rod so as to align the distal end of the connecting rod with the opening in the sidewall of the long arm screw tower that the connecting rod is to be received in during use. A tower channel may be provided on the rod reduction tool between the elongate alignment extension member and the elongate shaft of the rod reduction tool, so that when the elongate shaft is inserted into the a longitudinal channel of the misaligned long arm screw tower (e.g., the second long arm screw tower), a tower portion (e.g., the sidewall of the long arm screw tower) of the long arm screw tower resides within the tower channel of the rod reduction tool, so that the elongate shaft of the rod reduction tool is inside the long arm screw tower, and the alignment extension member is outside of the long arm screw tower, with the tower portion of the long arm screw tower portion in between.

In this orientation, rotation of the proximal handle portion of the rod reduction tool by the surgeon presses the paddle against the distal leading end of the connecting rod, urging it into the opening in the sidewall of the long arm screw tower (i.e., and down into the seating slot), as desired. Thus, another aspect of the present disclosure relates to a method for using such a rod reduction tool to urge alignment of the distal leading end of the connecting rod with the opening in the sidewall of the long arm screw tower, where the two are initially misaligned. Such a method may include providing such a rod reduction tool, and inserting the elongate shaft of the rod reduction tool into the misaligned long arm screw tower, so that the alignment extension member and paddle remain outside of the long arm screw tower. The paddle may be disposed on a side of the opening of the long arm screw tower, and may be pressed against the distal leading end of the connecting rod to urge it into the opening of the long arm screw tower. Such urging by the paddle may be achieved by rotating the proximal handle portion of the rod reduction tool to rotate the paddle towards the opening, pressing against the connecting rod, urging the distal leading end of the connecting rod into the opening of the long arm screw tower. In an embodiment, the rod reduction tool may be keyed relative to the long arm screw tower into which it is inserted, so that the long arm screw tower only accepts the elongate shaft of the rod reduction tool in a specific orientation, and so that once inserted, the two rotate together relative to the pedicle screw disposed distal to the long arm screw tower. Thus, the rod reduction tool and long arm screw tower may be rotated together, relative to the pedicle screw, and also relative to the connecting rod. This allows the desired alignment and insertion to be achieved between the distal leading end of the connecting rod and the opening in the sidewall of the long arm screw tower, permitting the distal leading end of the connecting rod to become seated in the seating slot of the long arm screw tower (e.g., the second "last" long arm screw tower).

While described with an elongate shaft that may be received into the long arm screw tower, other embodiments of rod reduction tools may be inserted over a long arm screw tower (or other PAD), rather than necessarily including an elongate shaft received therein. For example, various other mechanisms may be provided for engaging with the long arm screw tower (either internally, externally, or both), so that a paddle of the rod reduction tool may be disposed adjacent the opening into which the rod is to be urged, where the paddle can press against the rod or otherwise urge the rod and opening into proper alignment one with another.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 2C is a perspective view similar to that of FIG. 2B, but showing the rod in the first orientation;

FIG. 2D is a perspective view showing how the connecting rod may be rotated within the clamping mechanism of the rod delivery tool, and due to the curvature of the connecting rod, the leading end of the connecting rod can assume various positions;

FIG. 8C shows advancement of locking nuts through the other long arm screw towers, securing the connecting rod into the seating slots of each of the long arm screw towers;

FIG. 9A shows cutting or other removal of the connecting bridge at the tops of the long arm screw towers, and removal of the proximal portion of the first long arm screw tower (e.g., with a breakaway tool);

FIGS. 10A-10B show perspective views of two differently configured (e.g., right and left) rod reduction tools for use in urging alignment of a connecting rod and a given long arm screw tower;

DETAILED DESCRIPTION OF THE PREFERRED EMBODIMENTS

I. Introduction

Figure 1:
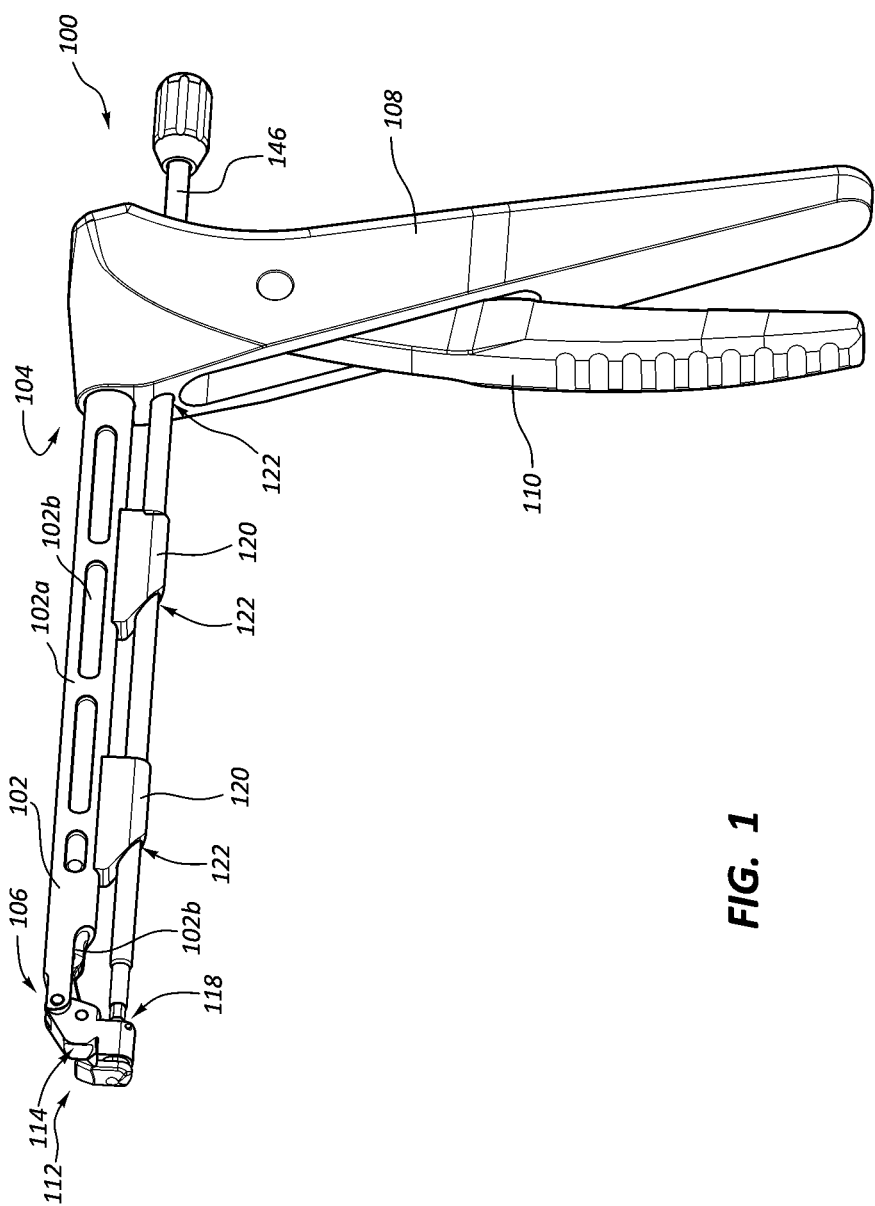
FIG. 1 is a perspective view of an exemplary rod delivery tool according to an embodiment of the present invention.

The present invention relates to methods and tools for delivery of a connecting rod of a pedicle screw system into seating slots of a plurality of long arm screw towers of the pedicle screw system, after pedicle screws of the system have been placed into pedicles of a patient's vertebrae. Such a method may include attaching a proximal end of a connecting rod to a rod delivery tool through a clamping mechanism of the rod delivery tool (e.g., at a distal end of an elongate shaft of such a rod delivery tool). An incision may be formed or otherwise provided next to a first long arm screw tower, providing a pathway through which the proximal end of the connecting rod may be delivered down to the distal end of the long arm screw tower. Such an incision is helpful as the connecting rod may not be inserted lengthwise down the long arm screw tower, but in a manner such that at least a portion of the connecting rod advances downward outside of the long arm screw tower, through the incision.

An elongate shaft of the rod delivery tool may be inserted through the first long arm screw tower, while at least a portion of the connecting rod remains outside of the first long arm screw tower, as the connecting rod is advanced downward, towards the distal end of the long arm screws, where the pedicle screws are anchored into the pedicle bone structure. The connecting rod may be in a first orientation relative to the elongate shaft of the tool, and/or relative to the hollow interior longitudinal channel of the long arm screw tower during insertion. At some point while advancing the connecting rod towards the pedicle screws, the connecting rod may be pivoted from the first orientation to a second orientation. For example, in the first orientation during initial advancement, the connecting rod may be relatively more vertically oriented, pivoting to a relatively more horizontal orientation in which it passes through both first and second long arm screw towers, linking them together through the connecting rod. Even in the first orientation, the connecting rod may be oriented so as to be transverse to the elongate shaft and the hollow interior longitudinal channel of the long arm screw tower, which may be received within one another. For example, the proximal "heel" end of the connecting rod may protrude through the sidewall of the long arm screw tower on one side of the long arm screw tower (e.g., the side on which the incision is formed), while the distal leading end of the connecting rod may protrude through the sidewall of the long arm screw tower on the opposite side of the long arm screw tower (e.g., 180° from the opening in the sidewall through which the proximal end protrudes).

At a desired position during advancement of the connecting rod towards the pedicle screws, the connecting rod may be pivoted from the first orientation towards the second orientation, pivoting the distal leading end of the connecting rod towards the second "last" long arm screw, so as to pass through the second long arm screw, as well as the first long arm screw. Once the distal leading end of the connecting rod is seated within a seating slot of the second long arm screw tower, a locking nut may be advanced distally through the second long arm screw tower, securing the distal leading end in place. The proximal "heel" end of the connecting rod may be released from the clamping mechanism of the rod delivery tool, and the rod delivery tool withdrawn from the first long arm screw tower. A locking nut may then be advanced distally through the first long arm screw tower to secure the proximal end of the connecting rod in place.

Another aspect of the present invention is directed to a rod delivery tool that may be used in the described method, for delivering such a connecting rod to the pedicle screws of the pedicle screw system. Such a tool may include an elongate shaft configured for receipt into the hollow interior longitudinal channel of any of the long arm screws, and a handle at a proximal end of the shaft. The handle may include a trigger or other actuating mechanism for pivoting the clamping mechanism and/or a connecting rod clamped therein from the first orientation to the second orientation. In addition to such a clamping mechanism at a distal end of the elongate shaft, the tool may further include one or more alignment guides disposed along a length of the elongate shaft for reception of a driver for selectively clamping or releasing the clamping mechanism (e.g., a screw thereof) about the connecting rod when a proximal heel end of the rod is received therein. Such alignment guides may define a driver channel through which the driver may be inserted (e.g., spaced apart and parallel to the elongate shaft of the tool), to loosen or tighten the grip on the connection rod.

The connecting rod may be held in the tool in an orientation that is transverse to the elongate shaft of the tool, in both the first and second orientations of the connection rod. In the first orientation, the transverse angle between the connecting rod and the elongate shaft of the tool (as well as between the rod and the channel of the long arm screw) may be relatively more shallow, but still transverse one relative to the other. In the second orientation, the transverse angle between the two may be greater (e.g., closer to perpendicular). The connecting rod may be held in the clamping mechanism in a manner so that the proximal heel end of the rod is not coaxial with the elongate shaft of the tool, but offset therefrom, in addition to the rod itself being transverse to the shaft and long arm screw channel. Because the connecting rod is offset relative to the elongate shaft, when the elongate shaft is inserted into the long arm screw tower, at least the proximal heel end of the connecting rod remains outside of the long arm screw tower.

Another aspect of the present disclosure relates to a rod reduction tool and a method of use thereof, for use in urging a connecting rod into alignment with an opening of a long arm screw tower that is initially misaligned relative to the distal leading end of the connecting rod. Such a rod reduction tool may include an elongate shaft extending from a proximal handle portion, the elongate handle being configured for receipt into a longitudinal channel of the long arm screw tower during use. An alignment extension member (also elongate) and including a paddle at a distal end thereof may be provided, also extending from the proximal handle portion. The paddle may be configured to engage and press the distal leading end of a connecting rod into alignment with an opening of a long arm screw tower during use. A tower channel may be provided radially outward, between the elongate shaft and the alignment extension member so that when the elongate shaft is inserted into the longitudinal channel of the long arm screw (e.g., the "last" long arm screw) during use, the tower portion (e.g., the sidewall) of the long arm screw tower resides in the tower portion of the reduction tool, with the elongate shaft inside the long arm screw tower, and the alignment extension member and paddle outside of the long arm screw tower. Rotation of the proximal handle portion may cause the long arm screw tower (and its sidewall opening) to rotate together, pressing the paddle against the distal leading end of the connecting rod, urging the two into alignment with one another so that the distal leading end of the connecting rod is received into the opening, as desired. This allows the distal leading end of the connecting rod to then be seated into the seating slot of the long arm screw tower.

II. Exemplary Methods and Devices

Figure 2B:
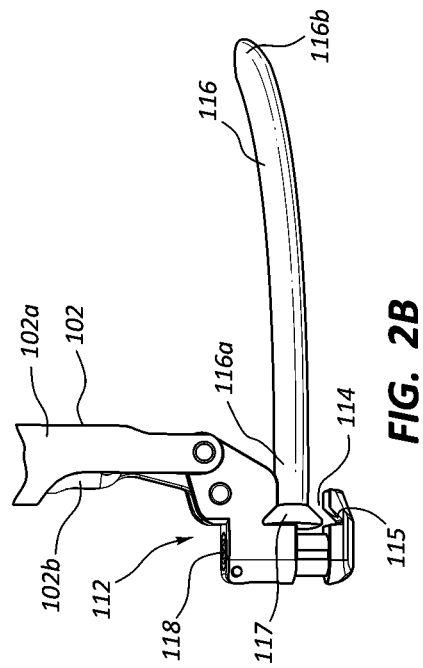
FIGS. 2A-2B are a perspective view, and close up perspective view, respectively, showing how a connecting rod may be clamped into the rod delivery tool of FIG. 1.
Figure 2A:
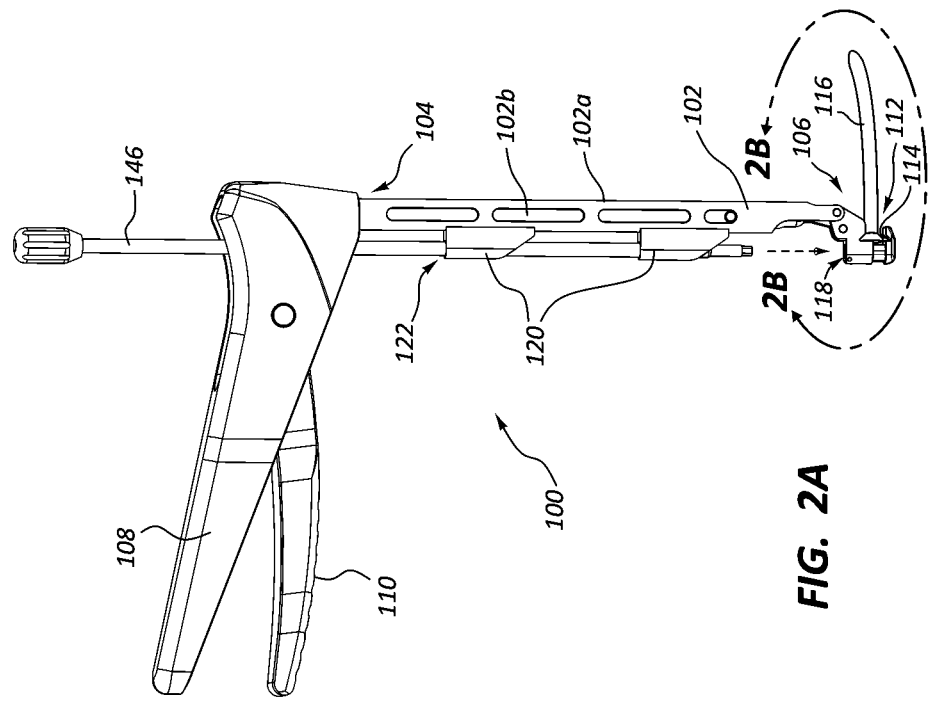
Figure 3:
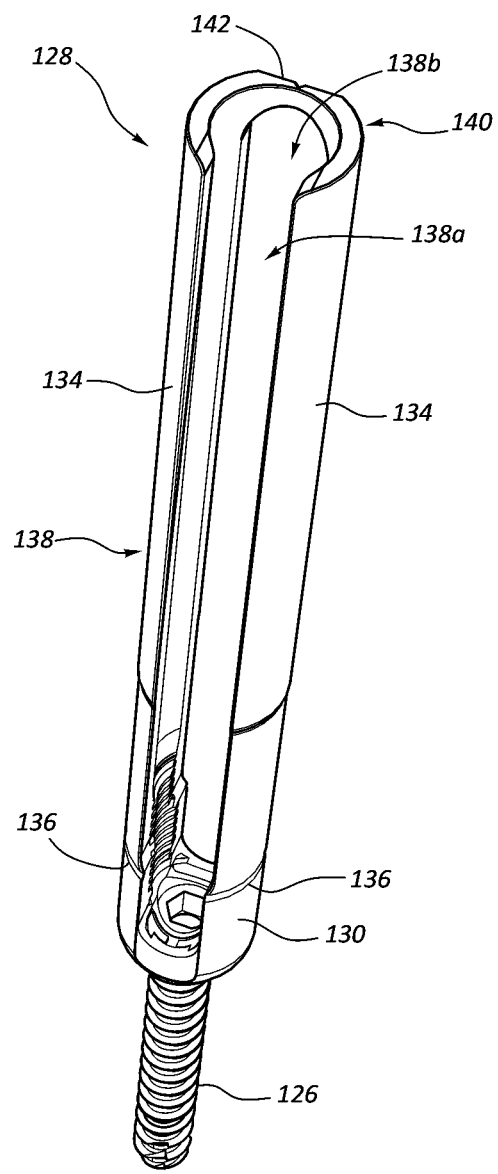
FIG. 3 is a perspective view of an exemplary long arm screw tower.

FIG. 1 shows an exemplary rod delivery tool 100 such as may be used in the presently described methods for delivering a connecting rod to a plurality of pedicle screws during a spinal fusion procedure. Tool 100 may include an elongate shaft 102 extending between proximal and distal ends 104, 106, respectively. Shaft 102 is sized and shaped so as to be received within a longitudinal channel of a long arm screw tower, as will be described in further detail below in conjunction with the methods shown beginning in FIG. 4. Such a long arm screw tower 128 is shown in FIG. 3. As seen in FIGS. 1-2D, tool 100 may further include a handle 108 at proximal end 104 of shaft 102. Handle 108 is shown as including an actuating mechanism, such as a trigger 110 for pivoting a clamping mechanism 112 at distal end 106 of shaft 102. Although shown with a trigger actuating mechanism 110, those of skill in the art will appreciate that the actuating mechanism is not particularly limited, and various other actuating mechanisms (e.g., other mechanical mechanisms such as buttons, knobs, levers, etc., and/or electrical or electromechanical mechanisms (e.g., touch button, touch screen, etc.)) may be suitable for use.

Clamping mechanism 112 is shown as being pivotally attached to distal end 106 of shaft 102. FIGS. 2A and 2B better illustrate the various structures of the clamping mechanism 112. Illustrated clamping mechanism includes a receptacle 114 into which connecting rod 116 may be selectively clamped. A clamp screw 118 may be provided for adjusting the width of receptacle 114, so that connecting rod 116 is selectively clampable and releasable within receptacle 114, upon adjustment (e.g., advance or retraction) of screw 118. As shown, receptacle 114 may include a recess 115, while the proximal end of rod 116 may include an enlarged heel 117, as shown. The heel may be received within recess 114. Because heel 117 is of the same shape around its full perimeter, heel 117 may advantageously be rotated within receptacle 114 to any desired orientation for clamping therein. Screw 118 may be in an end of clamping mechanism 112 so as to be accessible to a driver 146 (e.g., separate from tool 100), which can be coupled into screw 118 (e.g., a hex head screw), to adjust a dimension (e.g., width) of receptacle 114, selectively clamping or releasing the outside diameter of the proximal end of connecting rod 116 in receptacle 114. As shown, screw 118 may not actually contact rod 116, but rather may serve to widen and/or narrow the dimension of receptacle 114 as screw 118 is tightened or loosened.

Figure 5A:
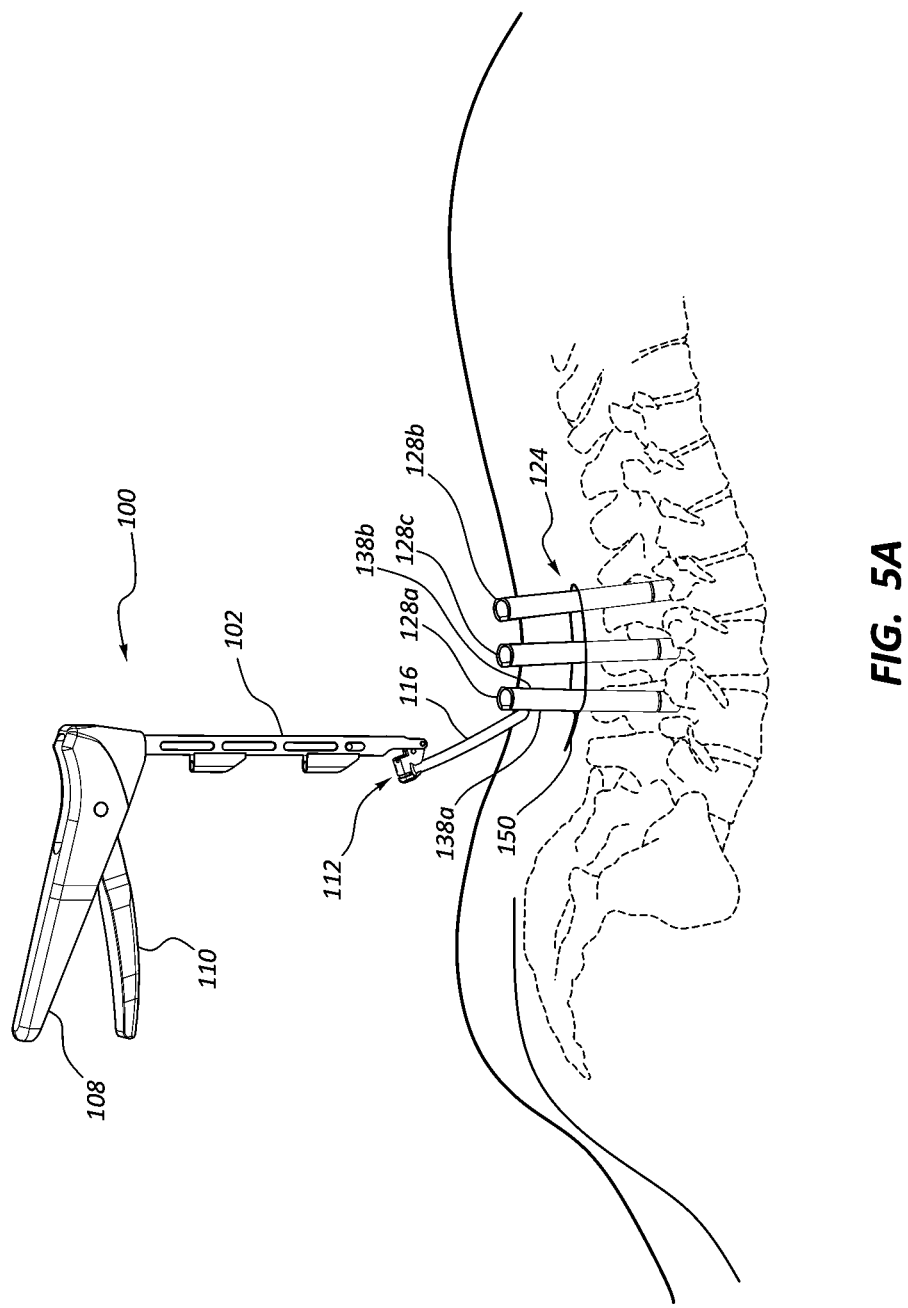
FIG. 5A shows preparation for insertion of an elongate shaft of the rod delivery tool into the first long arm screw tower.

Clamping mechanism pivots from a first orientation to a second orientation, causing a connecting rod 116 received therein to also pivot from its first orientation to its second orientation. FIGS. 1-2B and 2D illustrate the second orientation. FIGS. 2C and 5A illustrate the first orientation. As will be described in further detail below, the first orientation of the connecting rod 116 is helpful as the surgeon initially advances the connecting rod from outside the patient's body, downwards into the surgical site, towards the pedicle screws. Once inserted to a desired position, the trigger or other actuating mechanism 110 is actuated, pivoting the connecting rod 116 to its second orientation, for passage through the plurality of long arm screw towers. This sequence will be described in further detail below.

Figure 8A:
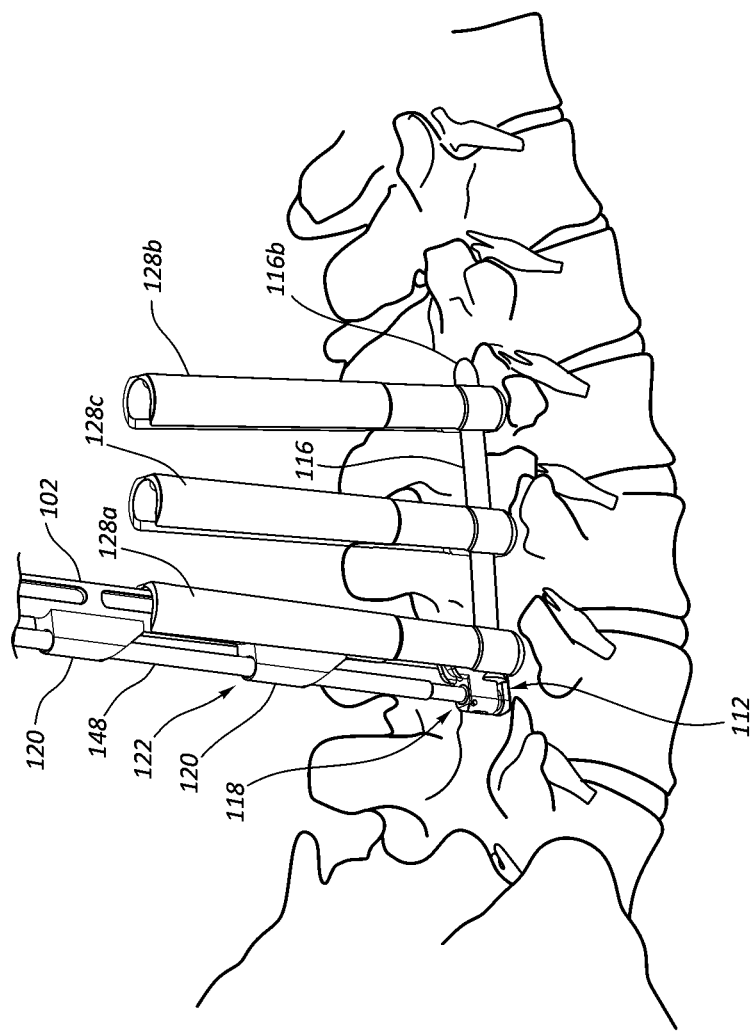
FIG. 8A shows insertion of a driver tool through one or more alignment guides disposed along a length of the elongate shaft of the rod delivery tool to release the clamping mechanism which secures the connecting rod to the rod delivery tool.

As seen in FIG. 1, the tool 100 is further shown as including one or more alignment guides 120 disposed along a length of elongate shaft 102. For example, as illustrated, alignment guides 120 may be disposed on a given side of shaft 102, e.g., the same side as clamping mechanism (e.g., where clamping mechanism 112 may be offset relative to the longitudinal axis of shaft 102). Illustrated alignment guides 120 include channels 122 disposed therethrough, so as to accommodate passage therethrough of a driver 146 for adjusting screw 118 of clamping mechanism 112. Channels 122 are axially aligned with the head (e.g., hex head) of screw 118 when clamping mechanism 112 is pivoted to its second orientation, allowing a driver to be inserted through channels 122 into the head of screw 118. When in the first orientation (FIG. 2C), the access surface to screw 118 may rotate counter-clockwise towards shaft 102. A channel 122 may also be formed through handle 108 and/or trigger 110, also aligned with channels 122 of alignment guides 120. Such a configuration allows the driver 146 for loosening (or tightening) clamping mechanism 112 about connecting rod 116 to be inserted through the proximal end 104 of tool 100, through handle 108, trigger lever 110, channels 122 of guides 120, and into head of screw 118 (when mechanism 112 is in the second orientation). FIG. 8A illustrates insertion of such a driver, so as to be generally parallel with shaft 102, during use in order to loosen rod 116.

As shown in FIG. 2D, the illustrated clamping mechanism 112 is particularly advantageous over various alternative mechanisms, as it allows up to full 360° rotation of connecting rod 116 within receptacle 114. For example, there may be no keyed alignment required between receptacle 114 of mechanism 112 and rod 116. Where connecting rod 116 is curved, as may typically be the case, it will be appreciated that the distal leading end of rod 116 may assume one of a variety of different positions, as the proximal heel end 116a is rotated within receptacle 114. As will be described in further detail below (e.g., particularly in conjunction with FIG. 11C), this clamped connection mechanism about the relatively smooth exterior outside diameter of proximal end of connecting rod 116 permits the surgeon to adjust the position and orientation of the connecting rod 116 within clamping mechanism 112, which can aid greatly when attempting to align and introduce the leading end of rod 116 through the various long arm screw sidewalls. Another distinct advantage of the illustrated configuration is that the surgeon may select the particular alignment desired by the rod within the clamping mechanism 112, before clamping the rod 116 into the mechanism 112. Such is not possible with existing systems, which include a recess or other keyed relationship between the rod and a clamping mechanism. This permits the surgeon to orient the rod in a custom selected orientation, depending on the specific placement of the long arm screw towers and pedicle screws, which can make it easier for the surgeon to "thread the needle" of the rod through each of of the long arm screw towers.

In a typical orientation of rod 116, the rod 116 may be clamped within mechanism 112 so that the concavely curved "inside" surface or a curved connecting rod 116 is oriented towards the remainder of tool 100 (e.g., shaft 102) when pivoted to the second orientation, as shown in FIG. 2B. When so oriented, the concavely curved surface of rod 106 may face an axis of elongate shaft 102. Stated another way, if rod 116 were sufficiently long (e.g., extrapolating the length of the rod), its leading end 116b would intersect an extrapolated axis of the elongate shaft 102, when in the first orientation, as seen in FIG. 2C. In other words, such an orientation of the rod 116 in receptacle 114 turns the leading end of the rod back towards the proximal end 104 of tool 100. Of course, as described in conjunction with FIG. 2D, the surgeon has the flexibility to choose a different rotational orientation of the rod 116 within receptacle 114, to better accommodate the need to insert rod 116 through the openings in the sidewalls of the long arm screws, depending on the specific placement or orientation of a given long arm screw tower.

As shown in FIGS. 1-2D, the elongate shaft 102 may include an outer sleeve 102a and an interior shaft 102b configured to slide axially within the outer sleeve 102a upon actuation of the actuating mechanism 110. As perhaps best seen in FIGS. 2B-2D, the interior shaft 102b may be coupled to the clamping mechanism 112 (e.g., through an elongate bar 102c), so as to cause the clamping mechanism 112 to pivot towards the second orientation as the interior shaft 102b slides axially within the outer sleeve 102a.

FIG. 3 illustrates an exemplary long arm screw tower 128, including opposed tower portions 134 extending upwardly from tulip head 130, with a groove or other break line 136 between the tower portion 134 (which is eventually removed) and tulip head 130 (which remains implanted in the patient). As shown, the long arm screw towers 128 may be configured to be open on two sides, through sidewalls 138 defining tower portions 134. At the proximal end of long arm screw tower 128, one open side may be open through top surface 140, while a connecting bridge 142 may be provided between tower portions 134 on the other side of long arm screw tower 128. As shown, one of openings (i.e., opening 138a) is shown as open at the top end of long arm screw tower 128, while the other opening (138b) is shown as including bridge 142 at the top, across tower portions 134, connecting the two tower portions at the top thereof on one side.

Figure 7:
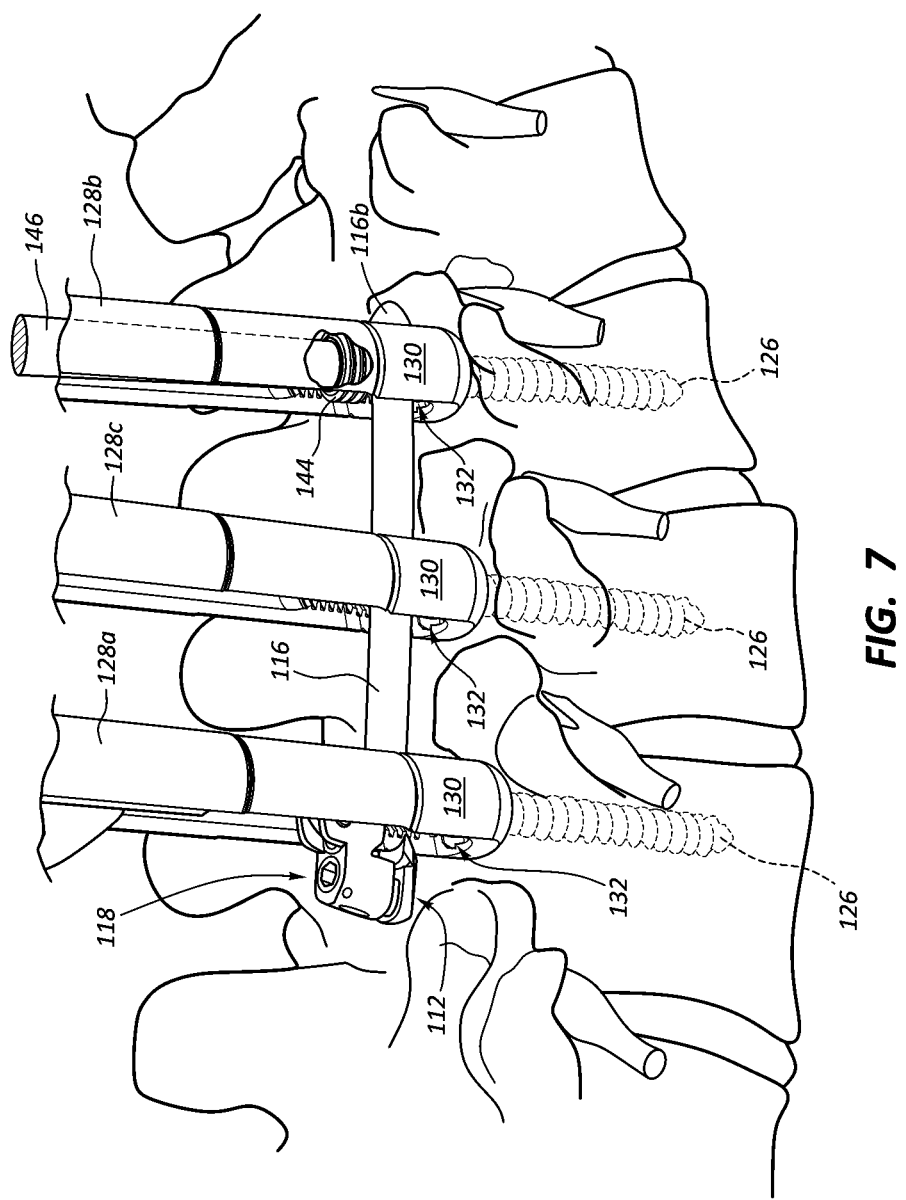
FIG. 7 shows advancement of a locking nut through the long arm screw tower over the distal leading end of the connecting rod to secure the distal leading end of the connecting rod into the seating slot of the second long arm screw tower.

The long arm screw tower 128 may be rotatable relative to its associated pedicle screw (e.g., screw 126 see FIG. 7). Because of this, the long arm screw tower 128 may be rotated to any desired orientation relative to pedicle screw 126 after pedicle screw 126 has been placed into the patient's pedicle bone structure. This provides the surgeon great flexibility in orienting the long arm screw towers as desired to be in the best possible alignment with a connecting rod 116 during placement of the rod 116.

Because the top 140 of long arm screw tower 140 is open on one side, as clearly seen in FIG. 3, it is particularly well suited for use with the rod delivery tool 100, in which the clamping mechanism 112 is not aligned with the elongate shaft 102, but offset therefrom. Alignment guides 120 are similarly offset from shaft 102, so that while shaft 102 may pass down the hollow interior longitudinal channel of the long arm screw tower 128, clamping mechanism 112 and guides 120 would run into a closed or bridged top 140, when attempting to insert shaft 102 into long arm screw tower 128. Because of the opening 138a reaching to top 140, accommodation of mechanism 112 and guides 120 is possible.

In a similar manner, the long arm screw tower 128 and rod reduction tool 200, described in further detail below, are also specifically configured to work together, as a result of the open top on one side of top 140 (i.e., at opening 138a). Specifically, tool 200 is shown as including a protrusion 214, which would similarly run into a closed top 140, but is able to slide down into open top 140 at opening 138a.

Because the connecting rod 116 is not passed through the long arm screw tower lengthwise, but at least the proximal end 116a passes through an incision next to the first long arm screw tower 128a, the system and method better accommodates the use of relatively longer rods, or rods with greater curvature than where passage through the long arm screw is required. For example, according to the present methods, a rod having a 10 inch radius of curvature may be employed. Such a curved rod, having a length of typically 3 to 3.5 inches, can be difficult to pass lengthwise through a percutaneous access device (PAD), as is done in other methods. This is particularly so if the rod is longer, and/or if the practitioner determines that greater curvature is needed. For example, a practitioner may often decide to increase the curvature in a portion of the rod to accommodate the specific anatomy of a given patient. Sometimes, such an altered rod may resemble a hockey stick, having a very sharp curvature towards one end. It can be nearly impossible to pass such a rod lengthwise through a PAD.

The present methods, tools, and systems advantageously more easily accommodate usage of such longer rods, or rods with relatively more curvature (e.g., having a radius of curvature of less than 10 inches). This is so because the connecting rod is not passed entirely through the long arm screw tower, but at least the proximal end is passed downward at a location that is next to the long arm screw tower. In addition, because the long arm screw tower includes openings 138a and 138b that are typically the vast majority of the length of the long arm screw tower, the opposite ends of the rod 116 are simply allowed to pass through either end of the long arm screw tower during advancement of the rod. This is a distinct advantage over the existing art.

Figure 4:
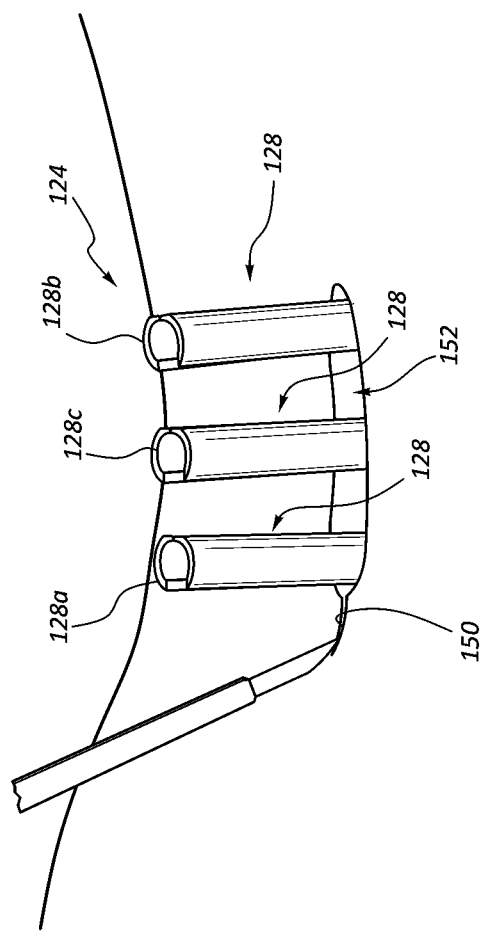
FIG. 4 is a perspective view showing a patient's back where a plurality of pedicle screws have been placed into pedicles of a patient's vertebrae, and in which a plurality of long arm screw towers are attached to the pedicle screws so as to extend out from the patient's back, where a scalpel is being used to cut an access opening for the connecting rod next to the first long arm screw tower.

Turning to FIG. 4, an exemplary method for delivery of connecting rod 116 that may employ tool 100 is illustrated. Prior to placement of connecting rod 116 of the pedicle screw system, a plurality of pedicle screws may have already been placed into pedicles of a patient's vertebrae. Placement of the pedicle screws may proceed according to any desired technique. Exemplary pedicle screws, "tulip" heads for such pedicle screws, depth measurement devices for aiding in selecting and placing an appropriate pedicle screw, and exemplary techniques for their use are described in the inventor's earlier U.S. Pat. Nos. 8,740,956; 9,084,633; 8,845,693; 8,986,318; and Published U.S. Applications 2015/0173844 and 2014/0148853. Each of the above patents and applications is herein incorporated by reference in its entirety. While use of such screws, other devices, and methods as described within the inventor's earlier work may be preferred, the present methods, devices, and systems are not limited to such, and any suitable devices, screws, and methods may be employed.

The pedicle screw system 124 may include pedicle screws 126, connecting rod 116, and a plurality of long arm screw towers 128 (e.g., see FIG. 7). The long arm screw towers 128 may include locking chucks and tulip heads 130, as described in U.S. Pat. No. 8,845,693, already incorporated by reference. Such locking chucks and/or tulip heads 130 may define seating slots 132 into which the connecting rod 116 may eventually be seated. A pedicle screw system 124 may include two or more pedicle screws 126, an equal number of long arm screw towers 128, and a connecting rod 116. The Figures show a system including three pedicle screws 126 (FIG. 7) and three long arm screw towers 128, although it will be appreciated that only two of each may be present, or more than three (e.g., four), or even more, may be present. Because only two may be present, the first long arm screw tower is referred to herein as first long arm screw tower 128a, and the "last" long arm screw tower is referred to herein as second long arm screw tower 128b. The middle or intermediate tower (which is optional) is referred to herein as a third long arm screw tower 128c. As described above, where long arm screw towers are rotatable relative to their underlying pedicle screws, this allows the surgeon to rotate the long arm screw towers 128 of FIG. 4 to any desired orientation. For example, they are shown with openings 138a all aligned to one side.

As shown in FIG. 4, before beginning to introduce connecting rod 116 into the surgical site and advancing it towards the pedicle screws, an incision 150 may be formed or otherwise provided adjacent to first long arm screw tower 128a. As the connecting rod 116 is not passed lengthwise down long arm screw tower 128a, but with at least a portion of rod 116 adjacent to, and outside tower 128a, incision 150 is helpful to accommodate the structures to be advanced therein. In other words, incision 150 provides a pathway for at least proximal end 116a of rod 116. As will be appreciated, the clamping mechanism 112 of tool 100 may also pass through the pathway of incision 150 during advancement of the connecting rod 116 towards the pedicle screws 126. By way of example, incision 150 may be formed after, or at the same time as one or more incisions through which the pedicle screws and long arm screw towers connected thereto are placed. FIG. 4 shows a single long incision 152 through which all of the long arm screw towers 128 and pedicle screws have been placed, although it will be appreciated that in another embodiment, a separate, shorter incision may be provided for each pedicle screw and associated long arm screw tower, with intact skin disposed between such adjacent relatively short incisions.

The additional incision 150 may be of any needed length so as to accommodate clamping mechanism 112 and rod 116. Rod 116 may be oriented generally vertically during initial advancement through incision 150, reducing the needed width. Of course, due to the curvature of the rod 116, it is not actually completely vertical. In addition, the actuating mechanism 110 and clamping mechanism 112 may be configured so that when the elongate shaft 102 of tool 100 is in fact vertical, the proximal heel end 116a of rod 116 may be offset therefrom and transverse thereto (e.g., at an angle of at least 3° relative to the shaft 102), even when in this substantially vertical first orientation of rod 116, seen in FIG. 2C. Incision 150 may typically have a length of from about 1 to 3 cm so as to accommodate the passage of clamping mechanism 112 and rod 116.

Figure 5B:
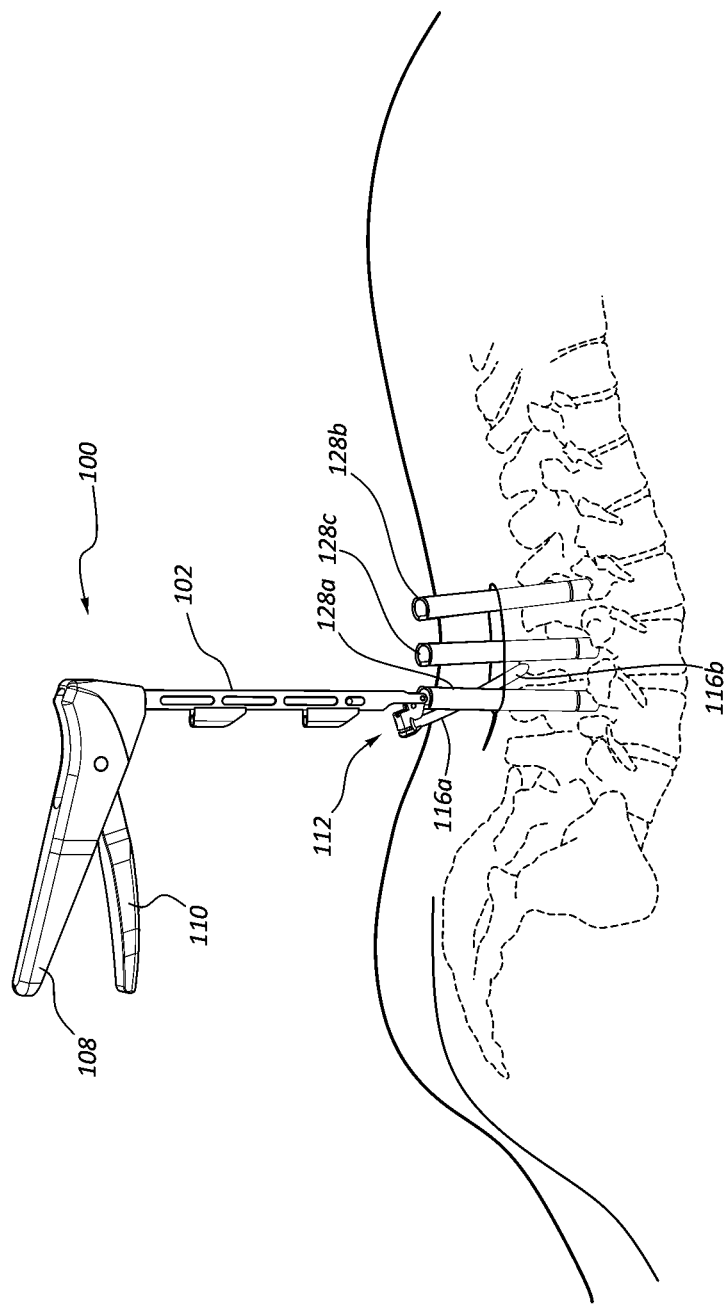
FIG. 5B shows the elongate shaft of the rod delivery tool being introduced into the first long arm screw tower, with the connecting rod being transverse to the long arm screw tower, a leading end of the connecting rod protruding through the sidewall of the long arm screw tower on one side, and the proximal heel end of the connecting rod protruding through an opposite sidewall of the long arm screw tower on the other side.
Figure 5C:
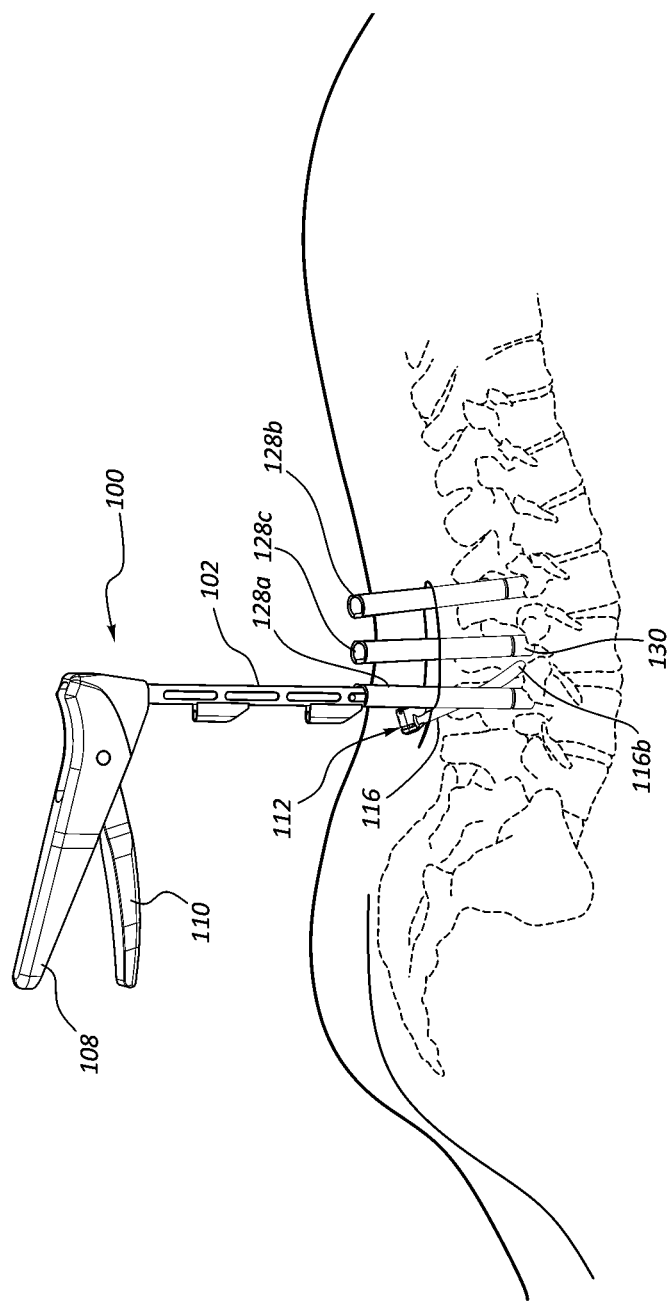
FIG. 5C shows further downward advancement of the elongate shaft of the tool into the first long arm screw tower, with further advancement of the connecting rod towards the pedicle screws.

As shown in FIGS. 5A-5C, once the incision 150 has been formed, the elongate shaft 102 of tool 100 may be prepared for insertion into first long arm screw tower 128a. As seen, connecting rod 116 may be clamped into clamping mechanism 112, with rod 116 in its first orientation, or even partially pivoted towards the second orientation according to the preference of the surgeon. Partial pivoting of rod 116 (by pressing trigger 110 or otherwise actuating the actuating mechanism) may be desired to swing the leading end 116b of rod 116 towards the opening 138a, which does not include any bridge across top surface 140, allowing elongate shaft 102 to be inserted into first long arm screw tower 128a, with clamping mechanism 112 passing through the unbridged opening at the top 140 of opening 138a. As will be apparent, because of bridge 142, this results in a "keyed" relationship, so that shaft 102 may only be inserted into long arm screw 128 in this one orientation, with clamping mechanism 112 (and rod 116) aligned over and with unbridged opening 138a. Unbridged opening 138a is open at the top, while opposite opening 138b is closed at the top, including a bridge 142, and may thus be termed a "slot", differing from open topped opening 138a. FIGS. 5B and 5C illustrate how mechanism 112 may slide downwards through opening 138a.

As shown in FIGS. 5B and 5C, once insertion begins, the connecting rod 116, in the first orientation, may be advanced downward towards the pedicle screws 126 at the distal ends of the long arm screw towers 128. As seen, during such advancement, at least a portion of rod 116 may remain outside of first long arm screw tower 128a. For example, the Figures show the proximal heel end 116a protruding outwardly, through opening 138a, while the distal leading end 116b protrudes outwardly through opening 138b in sidewall 138 defined by tower portions 134. While shown with a central portion of rod 116 inside the first long arm screw tower, it will be appreciated that the first orientation of the rod and clamping mechanism may allow the entire connecting rod 116 to be completely outside of the first long arm screw tower 128a, so that it is advanced down through incision 150, next to first long arm screw tower, adjacent opening 138a. Depending on the angulation provided by the clamping mechanism in the first orientation, just the distal leading end 116b of rod 116 may be in opening 138a, or within the hollow interior longitudinal channel of first long arm screw tower 128a, according to the preference of the surgeon. The illustrated configuration, with opposite ends of the rod 116 protruding out opposite ends of the openings 138a and 138b may be preferred.

FIG. 5C shows downward advancement having progressed so that distal leading end 116b of rod 116 has reached a level of tulip heads 130 (e.g., rod end 116b is shown adjacent tulip head 130 of third, "middle" long arm screw 128c). At a desired progression of insertion (e.g., such as this) the surgeon may actuate the actuating mechanism 110, causing the connecting rod 116 to pivot towards the second orientation, so as to pass the rod 116 through the adjacent long arm screw 128 (e.g., third, middle long arm screw 128c). Although three pedicle screws and three long arm screw towers are shown, it will be appreciated that any number of such may be provided. Typically, the number of such structures employed in a spinal fixation surgery is two to four.

Figure 6A:
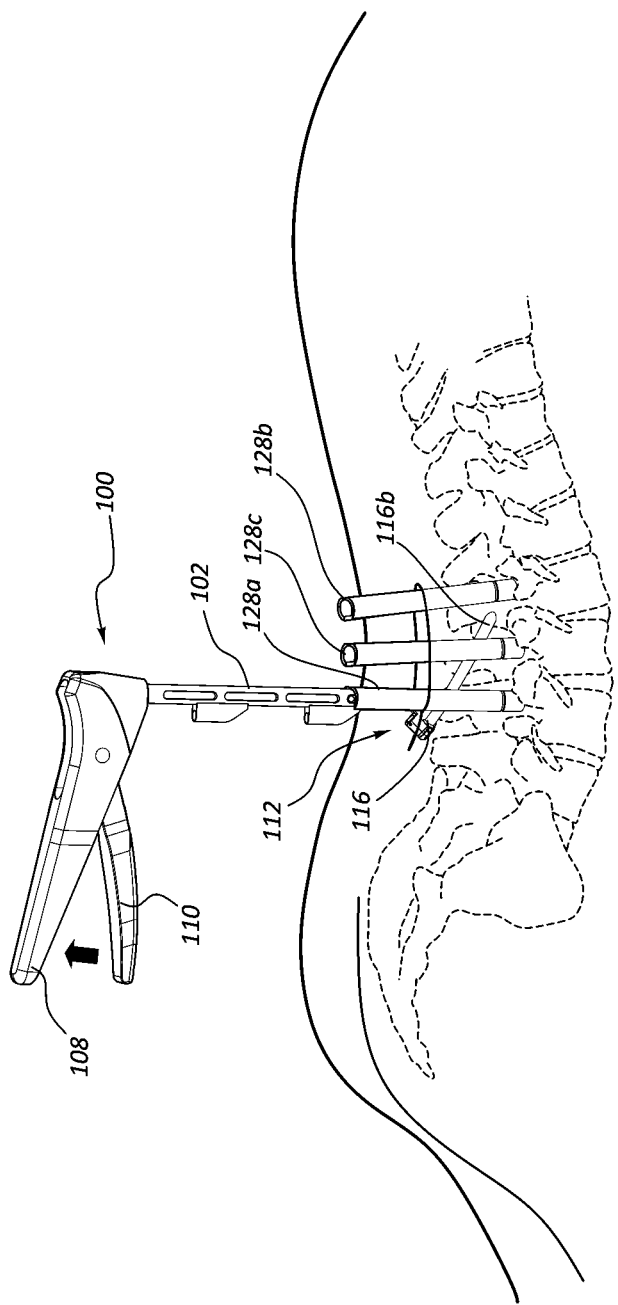
FIG. 6A shows actuation of the actuating mechanism (e.g., a trigger) on the handle of the rod delivery tool to begin to pivot the clamped connecting rod at the distal end of the elongate shaft of the rod delivery tool from a first orientation for insertion of the connecting rod towards a second orientation to facilitate passage of the connecting rod through the middle long arm screw tower.
Figure 6B:
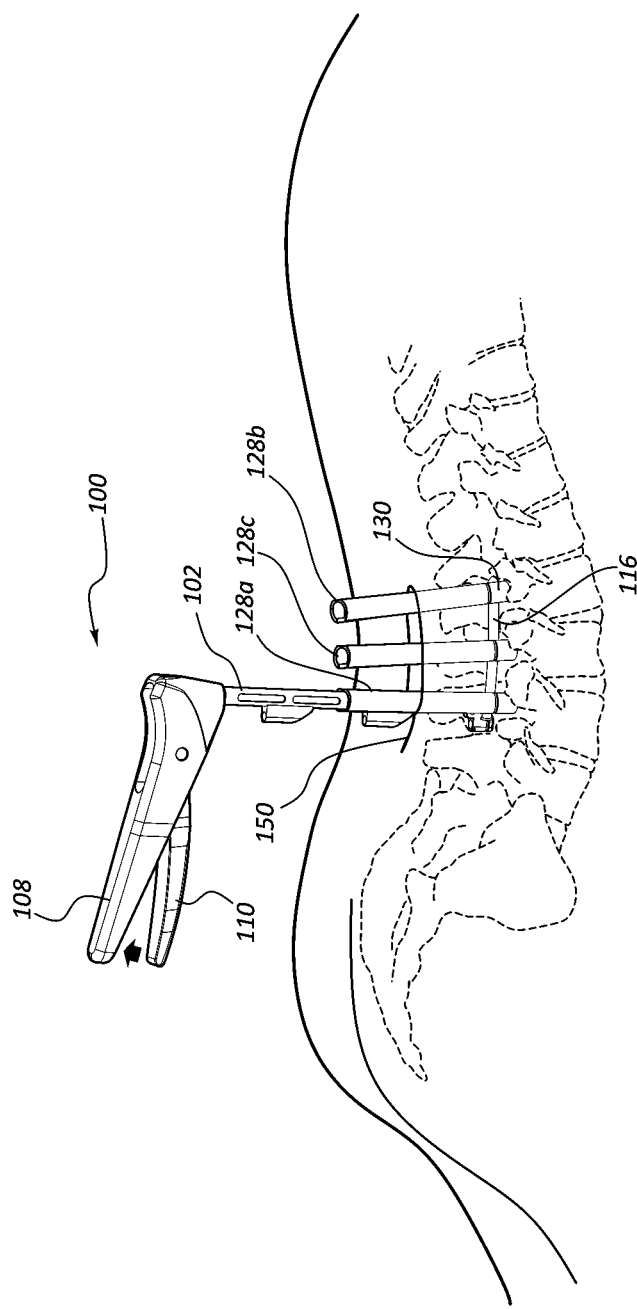
FIG. 6B shows further actuation of the actuating mechanism on the handle of the rod delivery tool, pivoting the clamped connecting rod to the second orientation, and in which the leading end of the connecting rod passes through all of the long arm screw towers.

FIG. 6A shows the connecting rod 116 being pivoted towards its second orientation, now passing through the adjacent long arm screw tower 128c. As shown in FIG. 6B, the rod 116 may continue to be pivoted towards the second orientation, so as to pass through the final long arm screw tower 128b. Depending on the preference of the surgeon, during such pivoting of rod 116, elongate shaft 102 may continue to be further advanced downward into first long arm screw tower 128a, as the distal leading end 116b of rod 116 swings towards the second (e.g., final) long arm screw tower 128b.

Once the connecting rod 116 spans all of the long arm screw towers (e.g., with rod 116 in or near the seating slots in the tulip heads 130 of each tower 128), the distal leading end 116b of rod 116 may be secured in the seating slot 132 defined by tulip head 130 of the long arm screw tower 128b. This may be accomplished by advancing a locking nut 144 associated with second long arm screw tower 128b distally, downward through tower 128b (e.g., using a locking nut driver 146), as seen in FIG. 7. The distal end of tower portion 134 and the proximal portion of tulip head 130 may include internal threading to accommodate screwing locking nut 144 over distal leading end 116b, securing it into place. At this stage, the proximal end 116a of rod 116 may still be clamped within clamping mechanism 112, and may or may not be fully seated against the bottom of the seating slot 132 of first long arm screw tower 128a.

Figure 8B:
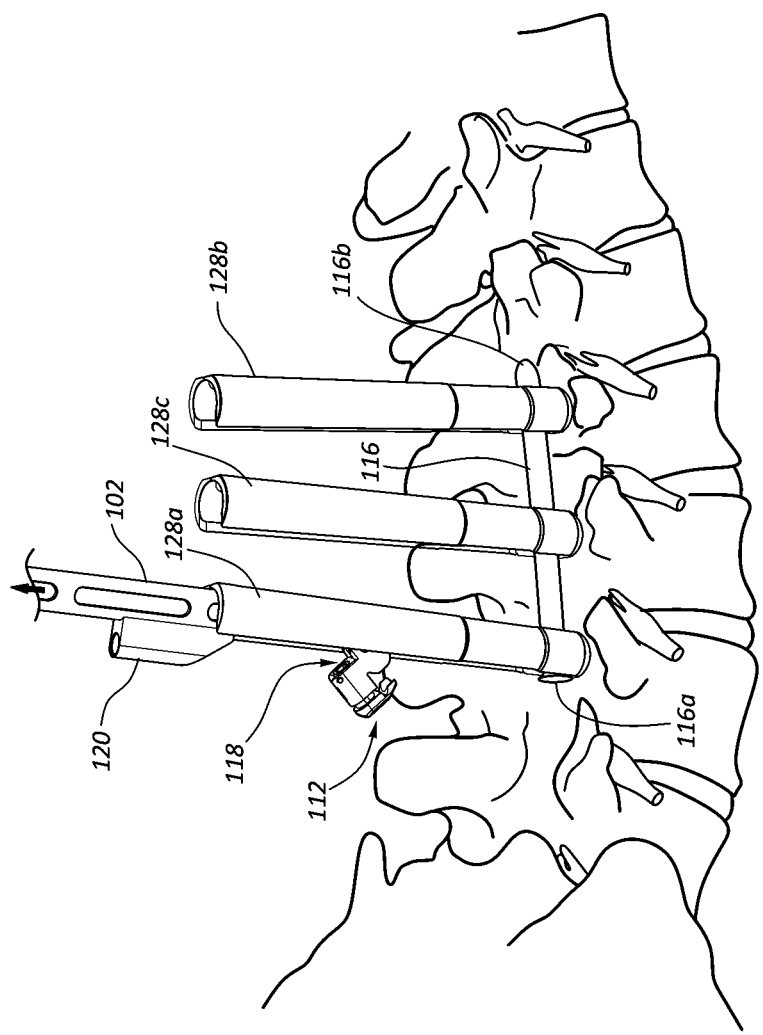
FIG. 8B shows removal of the rod delivery tool from the first long arm screw tower, leaving the connecting rod disposed through the long arm screw towers.

As seen in FIG. 8A, in any case, once leading end 116b is secured with locking nut 144, a driver 148 may be inserted through channels 122 of alignment guides 120, into the head of clamping screw 118. Rotation of driver 148 may loosen clamping mechanism 112, loosening the grip on rod 116, allowing release therefrom. Once rod 116 is loosened from clamping mechanism 112, the rod delivery tool 100 may be withdrawn, as shown in FIG. 8B. As shown in FIG. 8C, with tool 100 out of the way, a locking nut 144 may be advanced through first long arm screw tower 128a, securing the proximal end 116a of rod 116 in place. A locking nut 144 may also be advanced and secured over a central portion of rod 116, through the middle long arm screw tower 128c, where such a third (or fourth) long arm screw and pedicle screw are present.

Figure 9B:
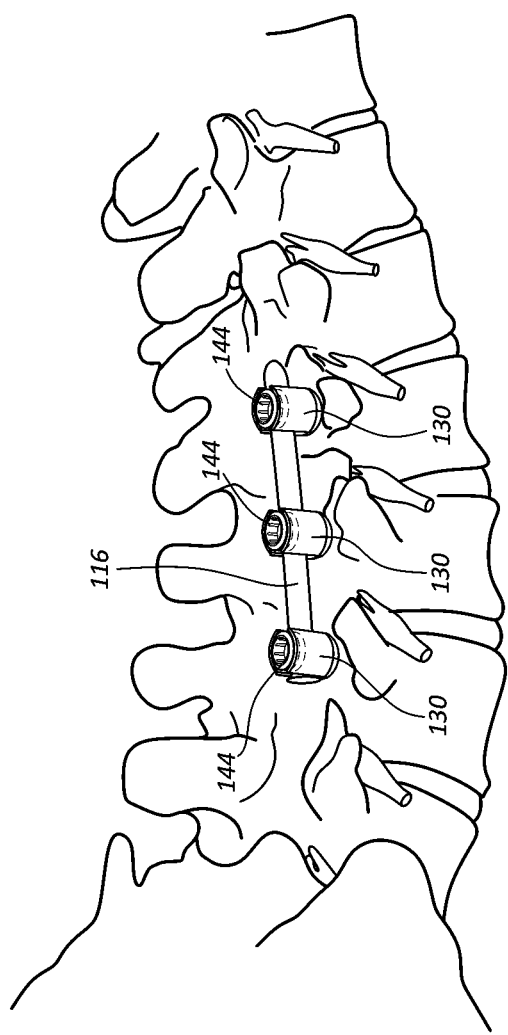
FIG. 9B shows removal of the proximal portions of each of the long arm screw towers.

Each of the locking nuts 144 may be further tightened to a desired force, e.g., 10 Nm. Any suitable tool such as a torque wrench (not shown), may be used for such purpose. The final tightened force applied to locking nuts 144 may be selected to ensure that the locking nuts and rod 116 remain in their desired positions within the installed pedicle screw system 124. Once the locking nuts 144 have been installed, the tower portions 134 of each of the long arm screw towers 128 may be removed. This may be achieved by cutting or otherwise removing the small connecting bridge 142 between tower portions 134, followed by inserting a suitable tab break away tool (not shown) over one of the tower portions, and bending it laterally outward, so that the tower portion snaps off at break line 136. FIG. 9A shows one tower portion 134 having been removed from the first long arm screw tower 128a, with the remaining tower portion 134 still to be removed. In FIG. 9B, all of the tower portions 134 have been removed from long arm screw towers 128, leaving just the tulip heads 130 of each of the long arm screw towers 128 in place.

Figure 11A:
FIG. 11A shows a scenario where the connecting rod is not aligned with each of the long arm screw towers, so that the surgeon may have difficulty introducing the connecting rod into one or more of the long arm screw towers (e.g., the last long arm screw tower)
Figure 11B:
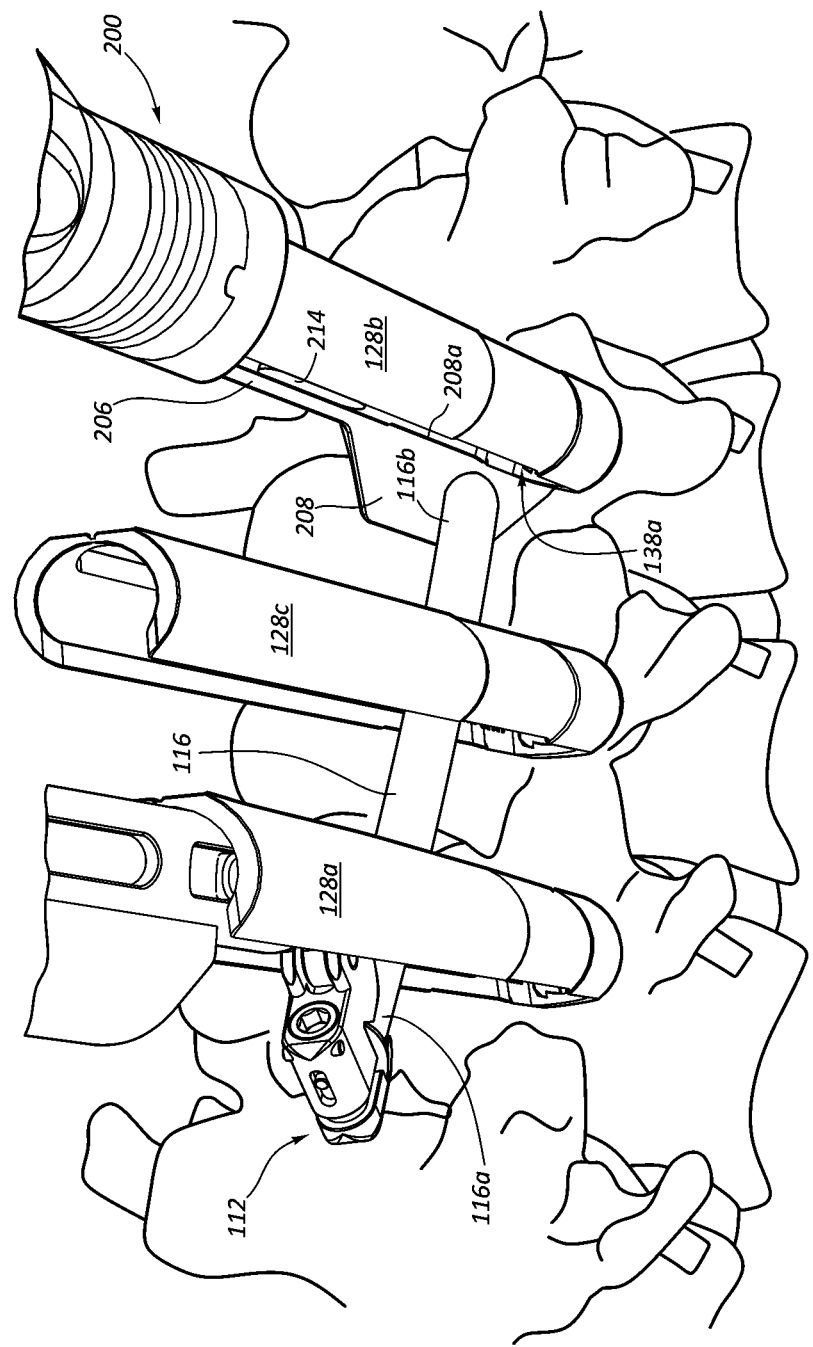
FIG. 11B shows how the elongate shaft of the appropriate rod reduction tool may be inserted into a long arm screw tower, and a paddle of the rod reduction tool may be used to push a leading end of the connecting rod into alignment so that it can be introduced into the opening in the sidewall of the long arm screw tower into which the elongate shaft of the rod reduction tool is inserted.
Figure 11C:
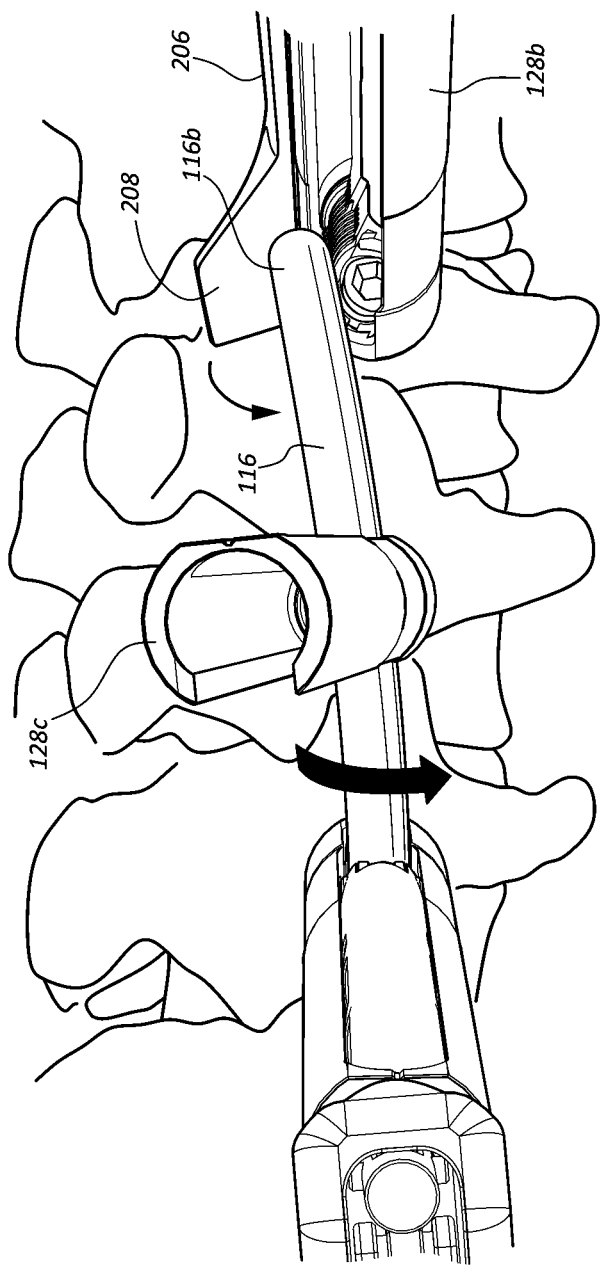
FIG. 11C shows how the proximal heel end of the connecting rod may be loosened within the clamping mechanism of the rod delivery tool, and then the paddle of the rod reduction tool used to push the leading end of the connecting rod, causing the rod to rotate as seen in FIG. 3, facilitating alignment and introduction of the leading end of the connecting rod into the long arm screw tower into which the elongate shaft of the rod reduction tool is inserted.

FIGS. 11A-11C illustrate use of a rod reduction tool 200 which may be helpful in urging the distal leading end 116b of connecting rod 106 into the openings between the towers 134 of any given long arm screw 128. FIGS. 10A and 10B show perspective views of exemplary rod reduction tools 200 and 200'. For example, particularly where three or more long arm screws and associated pedicle screws are employed in the spinal fusion, it may be difficult to achieve insertion of the leading end 116b of rod 116 through the final long arm screw tower 128b in the sequence of long arm screw towers 128. FIG. 11A illustrates such a scenario, where the connecting rod 116 has successfully passed through long arm screws 128a and 128c, but the leading end 116b is not aligned with opening 138a of long arm screw tower 128b.

FIGS. 10A-10B illustrate the exemplary rod reduction tools 200, 200', which are similar to one another. Tool 200 may be referenced, although it will be appreciated that tool 200' includes similar features. Rod reduction tool 200 includes an elongate shaft 202 extending from a proximal handle portion 204. Proximal handle portion may be enlarged, configured for being gripped by the surgeon during use, so that the surgeon may easily rotate tool 200. FIGS. 10A-10B show handle portion 204 including longitudinal recesses formed therein, for improved grip and torque in the surgeon's hand. Elongate shaft 202 may be aligned with a longitudinal axis of tool 200, so as to be centrally disposed, and extend distally from handle portion 204. Shaft 202 may be configured for insertion and receipt into the top of long arm screw tower 128 during use, similar to shaft 102 of rod delivery tool 100. While shown with a shaft 202 for receipt into a long arm screw tower, it will be appreciated that other engagement between the tool 200 and the long arm screw may be provided (e.g., a sleeve that fits over the top of the long arm screw tower, engaging externally and/or internally therewith, etc.). Such a sleeve may include an inwardly oriented projection (e.g., analogous to projection 214), that could engage within one of the sidewall openings of the long arm screw tower 128 (e.g., opening 138a). Such various alternative structures will be apparent to one of skill in the art in light of the present disclosure.

Tool 200 is shown as also including an alignment extension member 206 including a paddle 208 at a distal end of member 206. Alignment extension member 206 is also elongate, extending from proximal handle portion, but may be offset relative to a longitudinal axis of tool 200, as shown. Paddle 208 is shown as including a flat planar face 210 to press against the distal leading end 116b of a connecting rod 116, so as to urge the connecting rod 116 and the opening 138a of the long arm screw tower 128 into alignment with one another.

A tower channel 212 is shown as being provided between elongate shaft 202 and alignment extension member 206, so that a space exists between shaft 202 and member 206, into which one of tower portions 134 may be inserted during use of tool 200. Member 206 and paddle 208 are shown as being longer than shaft 202. For example, the length of member 206 and paddle 208 together may be approximately equal to that of the long arm screw tower that it is used with, so that when mated together, the paddle 208 reaches near or to the distal bottom end of the long arm screw tower 128b (e.g., to the bottom of unbridged opening 138a). As seen in FIGS. 11B-11C, when tool 200 is inserted into second long arm screw tower 128b, the elongate shaft 202 resides within the longitudinal channel of the long arm screw tower 128b, while alignment extension member 206 remains outside of the long arm screw tower 128b, with member 206 disposed against one of tower portions 134, tower portion 134 being in tower channel 212.

Elongate shaft 202 may further include a keyed protrusion 214, so that when elongate shaft 202 is inserted into the long arm screw tower, the keyed protrusion engages between tower portions 134 (in unbridged opening 138a). As a result of this keyed relationship, the generally oval shaped protrusion 214 engages with the ends of tower portions 134 defining opening 138a, preventing rotation of tool 200 relative to or within long arm screw 128. As a result, both structures rotate together. In other words, when the surgeon rotates proximal handle portion 204 of tool 200 with shaft 202 engaged in long arm screw 128, the long arm screw 128 will rotate with tool 200. As seen in FIGS. 11B-11C, the keyed protrusion 214 may be larger than the longitudinal channel of the long arm screw tower, so that protrusion 214 is not actually received into long arm screw tower 128, but slides along opening 138a, which is unbridged at its top, so as to accommodate sliding receipt of protrusion 214 therein. In this way, elongate shaft 202 is only receivable into the long arm screw tower 128 in this particular orientation, with opening 138a (unbridged at top) axially aligned with protrusion 214, so that tool 200 can slide into long arm screw tower 128 in this orientation, but not the opposite orientation (i.e., protrusion 214 hits bridge 142), or any other orientation (i.e., protrusion 214 hits tower portions 134). In other words, protrusion 214 and the adjacent portion of shaft 202 has a radius greater than the radius of the longitudinal channel of long arm screw tower 128, so that protrusion 214 cannot be received into the channel, only into the open topped opening 138a.

As seen, the keyed protrusion 214 may be oval shaped, although various other shapes are of course possible, to serve as a key for receipt into opening 138a. As shown, the alignment extension member 206 and paddle 208 may be on the same side, with paddle 208 (particularly paddle edge 208a) being generally aligned with an edge 216a of oval keyed protrusion 214. Thus, keyed protrusion 214 is received into opening 138a, while paddle 208 resides just to the side of opening 138a, where it can press against the distal leading end of the connecting rod 116, which is initially misaligned, pressing the opening 138a and connecting rod 116 into alignment with one another.

As shown, the alignment extension member 206 may include an internal surface 218 that is concavely curved so that the tower channel 212 is shaped to accommodate a convexly curved tower portion 134 of long arm screw 128.

FIG. 10A shows a left hand embodiment in which the alignment extension member 206 and paddle 208 are on the left side of the elongate shaft 202 to tool 200, to urge connecting rod 116 in a counter-clockwise direction relative to opening 138a in the sidewall 138 of long arm screw tower 128b during use. Depending on the particular misalignment of the distal leading end of the connecting rod 116, such a configuration may be useful for correcting the misalignment, and urging receipt of the distal leading end of the connecting rod 116 into the desired opening 138a. If the connecting rod is misaligned in the other direction, i.e., where clockwise rotation is desired, a right hand embodiment of a tool 200' that is otherwise similar to tool 200, but in which the alignment extension member 206' and paddle 208' (particularly paddle edge 208a') are positioned on the opposite side, aligned with the other edge 216b of keyed protrusion 214 may be used.

FIG. 11A shows a scenario where the distal leading end 116b of rod 116 is misaligned relative to opening 138a of second long arm screw tower 128b. FIG. 11B shows insertion of elongate shaft 202 of rod reduction tool 200 into the top 140 of second long arm tower screw 128b, with paddle 208 being used to push or otherwise urge distal leading end 116b of rod into the bottom of opening 138a. On occasion, even with such urging of paddle 208, it can be difficult to cause the desired alignment between distal leading end 116b and opening 138a of the second long arm screw 128b. As shown in FIG. 11C, the surgeon may choose to loosen the proximal heel end 116a of the rod 116, which will advantageously allow the rod 116 to rotate thereabout, as shown in FIG. 2D. With the proximal heel end 116a of rod 116 loosened, contact of paddle 208 against distal leading end 116b will typically easily facilitate the desired alignment. This may be particularly helpful in embodiments where the rod reduction tool locks with and rotates with the long arm screw tower, as rotation of paddle 208 may also actually rotate opening 138a. Because the rod 116 is loosened, it can rotate as shown in FIGS. 11C and 2D, causing the rod to align with opening 138a. Such an advantage of the ability to rotate the rod 116 about the proximal end provides valuable millimeters of lateral movement of the distal leading end, making it much easier for the practitioner to achieve the desired alignment. Such advantage is provided through the clamping mechanism 112 as described herein, which advantageously allows up to 360° rotation. Many existing rod delivery methods and systems simply do not provide such flexibility in orienting the rod, as needed for insertion into the various long arm screw towers.

Numbers, percentages, or other values stated herein are intended to include that value, and also other values that are about or approximately the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing process, and may include values that are within 25%, within 20%, within 10%, within 5%, within 1%, etc. of a stated value. Furthermore, the terms "substantially", "similarly", "about" or "approximately" as used herein represents an amount or state close to the stated amount or state that still performs a desired function or achieves a desired result. For example, the term "substantially" "about" or "approximately" may refer to an amount that is within 25%, within 20%, within 10% of, within 5% of, or within 1% of, a stated amount or value.

Ranges between any values disclosed herein are contemplated and within the scope of the present disclosure (e.g., a range defined between any two values (including end points of a disclosed range) given as exemplary for any given parameter).

As used in this specification and the appended claims, the singular forms "a," "an" and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for urging alignment of a distal leading end of a connecting rod with an opening of a long arm screw tower of a pedicle screw system where the connecting rod is misaligned for passage through the opening of the long arm screw tower, the method comprising:
   providing a rod reduction tool including:
      a proximal handle portion;
      an elongate shaft extending from said handle portion; and
      an alignment extension member also extending from said handle portion, said alignment extention member including at its distal end a paddle, the paddle being configured to engage and press the distal leading end of the connecting rod so as to align the distal leading end of the connecting rod with the opening in a sidewall of the long arm screw tower during use;
   engaging the rod reduction tool by placing it at least one of over or into the long arm screw tower where the distal leading end of the connecting rod is misaligned with the opening of the long arm screw tower, so that the alignment extension member and paddle remain outside of the long arm screw tower during engagement of the elongate shaft, the paddle being disposed on a side of the opening of the long arm screw tower against the distal leading end of the connecting rod;
   rotating the proximal handle portion of the rod reduction tool to urge the distal leading end of the connecting rod in a clockwise or counterclockwise direction relative to the longitudinal axis of said elongate shaft and into alignment with the opening in the long arm screw tower, so that the connecting rod is received into the opening of the long arm screw tower.

2. A method as in claim 1, wherein the alignment extension member and paddle are disposed on a given side of the opening in a sidewall of the long arm screw to urge the connecting rod in a clockwise direction relative to the longitudinal axis of the elongate shaft and into alignment with the opening in a sidewall of a long arm screw tower during use.

3. A method as in claim 1, wherein the alignment extension member and paddle are disposed on a given side of the opening of the sidewall of long arm screw to urge the connecting rod in a counter-clockwise direction relative to the longitudinal axis of the elongate shaft and into alignment with the opening in a sidewall of a long arm screw tower during use.

4. A method as in claim 1, wherein the elongate shaft is received into the long arm screw tower during use, the elongate shaft of the rod reduction tool including a keyed protrusion disposed thereon so that when the elongate shaft is inserted into the long arm screw tower the keyed protrusion engages between tower portions of a long arm screw tower so that the long arm screw tower rotates with the rod reduction tool.

5. A method as in claim 1, wherein a proximal end of the connecting rod passes through opposed openings in a first long arm screw tower, the long arm screw tower into which the elongate shaft of the rod reduction tool is engaged being a second long arm screw tower.

6. A method as in claim 5, wherein the proximal end of the connecting rod is received within a clamping mechanism of a rod delivery tool, an elongate shaft of the rod delivery tool being inserted into a hollow interior longitudinal channel of the first long arm screw tower.

7. A method as in claim 6, wherein the proximal end of the connecting rod is clamped within the clamping mechanism of the rod delivery tool.

8. A method as in claim 6, wherein the proximal end of the connecting rod is initially clamped within the clamping mechanism of the rod delivery tool, the method further comprising loosening the clamping mechanism about the connecting rod, so that the proximal end of the connecting rod can rotate within the clamping mechanism as the distal leading end of the connecting rod is urged into alignment with the opening in the second long arm screw tower.

9. A method for urging alignment of a distal leading end of a connecting rod with an opening of a long arm screw tower of a pedicle screw system where the connecting rod is misaligned for passage through the opening of the long arm screw tower, the method comprising:
    providing a rod reduction tool including:
        a proximal handle portion;
        an elongate shaft extending from said handle portion; and
        an alignment extension member also extending from said handle portion, said alignment extension member including at its distal end a paddle, the paddle being configured to engage and press the distal leading end of the connecting rod so as to align the distal leading end of the connecting rod with the opening in a sidewall of the long arm screw tower during use;
    engaging the rod reduction tool by placing it at least one of over or into the long arm screw tower where the distal leading end of the connecting rod is misaligned with the opening of the long arm screw tower, so that the alignment extension member and paddle remain outside of the long arm screw tower during engagement of the elongate shaft, the paddle being disposed on a side of the opening of the long arm screw tower against the distal leading end of the connecting rod; and
    rotating the proximal handle portion of the rod reduction tool to urge the distal leading end of the connecting rod in a clockwise or counterclockwise direction relative to the longitudinal axis of said elongate shaft and into alignment with the opening in the long arm screw tower, so that the connecting rod is received into the opening of the long arm screw tower;
    wherein a proximal end of the connecting rod passes through opposed openings in a first long arm screw tower, the long arm screw tower into which the elongate shaft of the rod reduction tool is inserted being a second long arm screw tower;
    wherein the proximal end of the connecting rod is received within a clamping mechanism of a rod delivery tool, an elongate shaft of the rod delivery tool being inserted into a hollow interior longitudinal channel of the first long arm screw tower.

10. A method as in claim 9, wherein the proximal end of the connecting rod is clamped within the clamping mechanism of the rod delivery tool.

11. A method as in claim 9, wherein the proximal end of the connecting rod is initially clamped within the clamping mechanism of the rod delivery tool, the method further comprising loosening the clamping mechanism about the connecting rod, so that the proximal end of the connecting rod can rotate within the clamping mechanism as the distal leading end of the connecting rod is urged into alignment with the opening in the second long arm screw tower.

\* \* \* \* \*